(12) United States Patent
Theodoridis et al.

(10) Patent No.: US 7,671,201 B2
(45) Date of Patent: *Mar. 2, 2010

(54) PHENYL SUBSTITUTED CYCLIC DERIVATIVES

(75) Inventors: George Theodoridis, Princeton, NJ (US); Edward J. Barron, Trenton, NJ (US); John W. Lyga, Basking Ridge, NJ (US); Y. Larry Zhang, Kendall Park, NJ (US); Ping Ding, Lawrenceville, NJ (US); Frank J. Zawacki, Yardley, PA (US); Daniel H. Cohen, Princeton, NJ (US); Matthew P. Whiteside, Morrisville, PA (US)

(73) Assignee: FMC Corporation, Philadelphia, PA (US)

( * ) Notice: Subject to any disclaimer, the term of this patent is extended or adjusted under 35 U.S.C. 154(b) by 957 days.

This patent is subject to a terminal disclaimer.

(21) Appl. No.: 10/554,328

(22) PCT Filed: Apr. 27, 2004

(86) PCT No.: PCT/US2004/012890

§ 371 (c)(1),
(2), (4) Date: Oct. 24, 2005

(87) PCT Pub. No.: WO2004/099145

PCT Pub. Date: Nov. 18, 2004

(65) Prior Publication Data

US 2006/0270726 A1 Nov. 30, 2006

Related U.S. Application Data

(60) Provisional application No. 60/466,674, filed on Apr. 30, 2003.

(51) Int. Cl.
*C07D 241/00* (2006.01)
*C07D 211/68* (2006.01)
*C07D 401/00* (2006.01)
*A01N 25/00* (2006.01)

(52) U.S. Cl. .................. 544/336; 546/194; 546/207; 424/405

(58) Field of Classification Search ........... 544/336; 546/194, 207; 424/405
See application file for complete search history.

(56) References Cited

U.S. PATENT DOCUMENTS

| | | | |
|---|---|---|---|
| 3,474,170 A | 10/1969 | Scharpf | |
| 3,474,171 A | 10/1969 | Scharpf | |
| 3,747,171 A | 7/1973 | Montague, Jr. | |
| 4,338,317 A | 7/1982 | Temple, Jr. et al. | |
| 4,487,773 A | 12/1984 | Temple, Jr. et al. | |
| 5,360,919 A | 11/1994 | Standen | |
| 5,639,763 A * | 6/1997 | Silverman et al. | ........... 514/321 |
| 5,872,137 A | 2/1999 | Sakamoto et al. | |
| 5,922,880 A | 7/1999 | Sakamoto et al. | |
| 5,952,386 A | 9/1999 | Matsuo et al. | |
| 6,028,100 A | 2/2000 | Matsuo et al. | |
| 6,063,734 A | 5/2000 | Ogura et al. | |
| 6,071,861 A | 6/2000 | Sakamoto et al. | |
| 6,214,835 B1 | 4/2001 | Matsuo et al. | |
| 6,268,313 B1 | 7/2001 | Sakamoto et al. | |
| 6,294,573 B1 | 9/2001 | Curtin et al. | |
| 6,376,428 B1 | 4/2002 | Sakamoto et al. | |
| 6,403,639 B1 | 6/2002 | Ishikawa et al. | |
| 6,407,243 B1 | 6/2002 | Bryant et al. | |
| 6,462,049 B1 | 10/2002 | Ogura et al. | |
| RE38,188 E | 7/2003 | Ogura et al. | |
| 6,589,914 B2 | 7/2003 | Sakamoto et al. | |
| 6,706,739 B2 | 3/2004 | Shia et al. | |
| 6,987,194 B2 | 1/2006 | Theodoridis et al. | |
| 7,208,450 B2 | 4/2007 | Theodoridis et al. | |
| 2003/0073847 A1 | 4/2003 | Sakamoto et al. | |
| 2004/0029886 A1 | 2/2004 | Tiebes et al. | |
| 2005/0159599 A1 | 7/2005 | Itoh et al. | |

(Continued)

FOREIGN PATENT DOCUMENTS

EP 0 648 729 A1 4/1995

(Continued)

OTHER PUBLICATIONS

Clough, J.M., et al., "Fungicidal β-Methyoxyacrylates," *Syn. Chem. Agrochem. ACS Symposium Series 504*, pp. 372-383 (1992).

(Continued)

*Primary Examiner*—Janet L. Andres
*Assistant Examiner*—John Mabry

(57) ABSTRACT

Certain novel phenyl substituted cyclic derivatives have unexpected insecticidal activity. These compounds are represented by formula I: where B is a cyclic bridging group containing at least one N or N oxide link and a, A, b, B, c, d, D, L, M, $R^1$ through $R^9$, inclusively, and $R^{13}$, $R^{14}$ and $R^{15}$ are fully described herein. In addition, novel intermediates useful in preparing compounds of Formula I, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present.

(I)

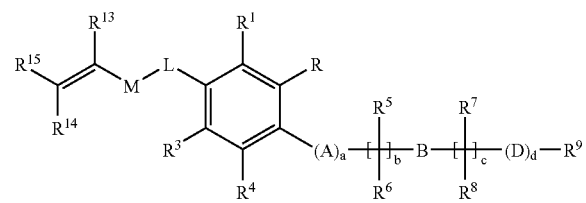

10 Claims, No Drawings

U.S. PATENT DOCUMENTS

| | | |
|---|---|---|
| 2005/0171356 A1 | 8/2005 | Theodoridis et al. |
| 2006/0094776 A1 | 5/2006 | Theodoridis et al. |
| 2006/0247283 A1 | 11/2006 | Theodoridis et al. |

FOREIGN PATENT DOCUMENTS

| | | |
|---|---|---|
| WO | WO 94/06782 A1 | 3/1994 |
| WO | WO 95/23507 A1 | 9/1995 |
| WO | WO 96/11909 A1 | 4/1996 |
| WO | WO 96/33160 A1 | 10/1996 |
| WO | WO 01/44154 A1 | 6/2001 |
| WO | WO 01/55141 A1 | 8/2001 |
| WO | WO 03/074498 A1 | 9/2003 |
| WO | WO 2004/006782 A1 | 1/2004 |
| WO | WO 2004/020445 A2 | 3/2004 |
| WO | WO 2004/056735 A1 | 7/2004 |
| WO | WO 2004/099145 A2 | 11/2004 |

OTHER PUBLICATIONS

Shia, K.-S., et al., "Design, Synthesis, and Structure—Activity Relationship of Pyridyl Imidazolidinones: A Novel Class of Potent and Selective Human Enterovirus 71 Inhibitors," *J. Med. Chem.* 45:1644-1655, American Chemical Society (2002).

Shiokawa, K., et al., "Chloronicotinyl Insecticides: Development of Imidacloprid," *Eighth Int. Congress of Pesticide Chem., ACS*, pp. 49-58 (1995).

International Search Report for International Application No. PCT/US05/17993, ISA/US, Alexandria, VA, mailed on Sep. 21, 2006.

Wells, K.M., et al., "Regioselective Nucleophilic Substitutions of Fluorobenzene Derivatives," *Tetrahedron Lett.* 37:6439-6442, Elsevier Science Ltd. (1996).

International Search Report for International Application No. PCT/US04/12890, ISA/US, Alexandria, VA, mailed on Oct. 25, 2004.

International Search Report for International Application No. PCT/US04/13023, ISA/US, Alexandria, VA, mailed on Jan. 25, 2005.

Database WPI, Accession No. 1996-263801, Japanese Patent 08 109156 A Abstract.

Supplementary European Search Report, European Patent Application No. EP 04 75 0775, European Patent Office, Munich, search completed on Nov. 30, 2007.

Supplementary European Search Report, European Patent Application No. EP 04 75 0769, European Patent Office, Munich, search completed on Sep. 17, 2007.

Supplementary European Search Report, European Patent Application No. EP 04 76 0587, European Patent Office, Munich, search completed on Sep. 17, 2007.

Supplementary European Search Report, European Patent Application No. EP 04 76 0588, European Patent Office, The Hague, search completed on Jul. 9, 2008.

* cited by examiner

PHENYL SUBSTITUTED CYCLIC DERIVATIVES

This application claims the benefit of U.S. Provisional Application No. 60/466,674, filed Apr. 30, 2003.

FIELD OF THE INVENTION

The present invention relates to novel compounds and their use in controlling insects and acarids. In particular, it pertains to phenyl substituted cyclic derivatives and agriculturally acceptable salts thereof, compositions containing them and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Insecticides and acaricides are useful for controlling insects and acarids which may otherwise cause significant damage to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of patents and publications disclose a variety of dihalopropene compounds that are reported to be insecticidally and acaricidally active. For example, U.S. Pat. No. 5,922,880 discloses certain dihalopropene compounds for use as insecticides and acaricides of the general formula:

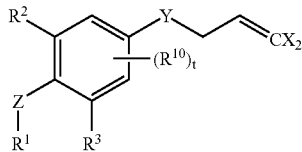

where Z is oxygen, sulfur, or $NR^4$ (wherein $R^4$ is hydrogen, or $C_1$-$C_3$ alkyl); Y is oxygen, sulfur, or NH; X's are independently chlorine or bromine; $R^2$, $R^3$, and $R^{10}$ are independently halogen, $C_1$-$C_3$ alkyl, or $C_1$-$C_3$ haloalkyl; t is an integer of 0 to 2; and $R^1$ is A-$(CR^5R^6)_p$CHR$^7$— (Q1), A-B—$(CR^5R^6)_p$CHR$^7$— (Q2), A-$(CR^{11}R^{12})_s$—B—$(CR^5R^6)_p$—CHR$^7$— (Q3), A-$C(R^{13})$=$C(R^{14})$—$(CR^5R^6)_p$—CHR$^7$— (Q4), A-B—$(CR^{11}R^{12})_s$—$C(R^{13})$=$C(R^{14})$—$(CR^5R^6)_p$—CHR$^7$— (Q5), A-B—$(CR^{11}R^{12})_s$—C(=O)—O—$(CR^5R^6)_p$—CHR$^7$— (Q6), or A-$C(R^{13})$=$C(R^{14})$—C(=O)—O—$(CR^5R^6)_p$—CHR$^7$— (Q7), where A is an optionally substituted heterocyclic ring; B is oxygen, $S(O)_q$, $NR^9$, $C(=G^1)G^2$ or $G^1C(=G^2)$; q is an integer of 0 to 2; $R^9$ is hydrogen, acetyl or $C_1$-$C_3$ alkyl; $G^1$ and $G^2$ are independently oxygen and sulfur; $R^5$, $R^6$, $R^7$, $R^{11}$ and $R^{12}$ are independently selected from hydrogen, $C_1$-$C_3$ alkyl, or trifluoromethyl; $R^{13}$ and $R^{14}$ are independently selected from hydrogen, $C_1$-$C_3$ alkyl, halogen or trifluoromethyl; p is an integer of 0 to 6; and s is an integer of 1 to 6.

U.S. Pat. No. 5,569,664 discloses compounds of the following structure as having insecticidal activity:

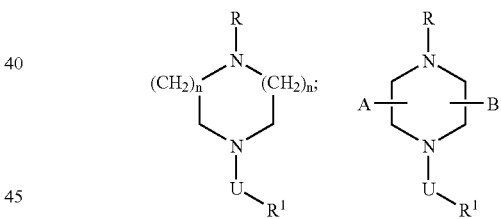

where U is selected from —$(CH_2)_n$— and ethylidine, where n is 1, 2, or 3; Q is selected from hydrogen, hydroxy, sulfhydryl, and fluorine; V is selected from hydrogen, halogen, alkyl, haloalkyl, alkoxy, alkylthio, alkylsulfinyl, alkylsilyloxy, dialkylamino, cyano, nitro, hydroxy, and phenyl; W is selected from hydrogen, halogen, alkyl, haloalkyl, alkoxy, nitro, amino, phenoxy, and phenylalkoxy; X is selected from hydrogen, hydroxy, halogen, alkyl, alkoxyalkyl, alkoxy, cycloalkylalkoxy, haloalkoxy, alkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkoxycarbonylamino, alkylcarbonyl, alkoxycarbonyl, alkylaminocarbonyl, aminocarbonyloxy, phenyl, phenylalkoxy, phenoxy, and phenoxyalkyl; Y and Z are independently selected from hydrogen and alkoxy; $R^1$ and $R^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and the corresponding N-oxides and agriculturally acceptable salts.

United States Statutory Invention Registration H2007 discloses compounds of the following structures as having insecticidal activity:

where A and B are independently selected from lower alkyl; U is selected from lower alkylidene, lower alkenylidene, and CH-Z, where Z is selected from hydrogen, lower alkyl, lower cycloalkyl, or phenyl; R is —$CHR^3R^4$ where $R^3$ and $R^4$ are independently selected from phenyl, optionally substituted with halogen, lower alkyl, lower haloalkyl, lower alkoxy, lower haloalkoxy, lower alkenyl, or phenyl; $R^1$ is phenyl, naphthyl, tetrazolylphenyl, phenylcyclopropyl, phenoxyphenyl, benzyloxyphenyl, pyridylphenyl, pyridyloxyphenyl, or thiadiazolyloxyphenyl, each optionally substituted with halogen, cyano, hydroxy, lower alkyl, lower haloalkyl, lower alkoxy, amino, lower dialkylamino, nitro, lower haloalkylsulfonyloxy, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic $R^1$ groups; m is 2 or 3; and n is 1, 2, or 3.

SUMMARY OF THE INVENTION

In accordance with the present invention, it has now been found that certain novel phenyl substituted cyclic derivatives are surprisingly active in the control of insects and acarids when used in the insecticidal and acaricidal compositions and methods of this invention. The novel phenyl substituted cyclic derivatives are represented by the following general formula I:

I where
—R and $R^4$ are independently selected from hydrogen, halogen, hydroxy, $(C_1-C_6)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-C_3)$alkylthio, $(C_1-C_3)$alkylsulfonyl, halo$(C_1-C_3)$alkylsulfonyl, cyano, nitro; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=E)-G, and —C($R^{10}$)-J-$R^{11}$, wherein the optional substituent is selected from $(C_1-C_4)$alkyl, halogen, halo$(C_1-C_4)$alkyl, $(C_1-C_4)$alkoxy, $(C_1-C_4)$alkoxy$(C_1-C_4)$alkyl, $(C_3-C_6)$cycloalkyl, $(C_2-C_5)$alkenyl, $(C_2-C_5)$alkynyl, cyano, nitro and aryl;

where
E is selected from O, S, $NR^{12}$, and $NOR^{12}$, where $R^{12}$ is hydrogen, $(C_1-C_4)$alkyl, halo$(C_1-C_4)$alkyl, aryl and aryl $(C_1-C_4)$alkyl;
G is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;
J is selected from O, S, and $NR^{12}$, where $R^{12}$ is as previously described;
$R^{10}$ and $R^{11}$ are independently selected from hydrogen, $(C_1-C_4)$alkyl and halo$(C_1-C_4)$alkyl, and $R^{10}$ and $R^{11}$ may be taken together with —K(CH$R^{12}$)$_e$—, where e is an integer of 2 to 4; K is selected from O, S, and $NR^{12}$, where $R^{12}$ is as previously described;
—$R^1$ and $R^3$ are independently selected from hydrogen, halogen and $(C_1-C_3)$alkyl;
-L is selected from selected from $CH_2$, O, S and $NR^{16}$ where $R^{16}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl $(C_1-C_3)$alkyl, halo$(C_2-C_4)$alkenyl$(C_1-C_3)$alkyl, di$(C_1-C_3)$alkylphosphonate, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl;
-M is selected from O, S, *OCH$_2$ and (CH$_2$)$_f$ where the asterisk denotes attachment to L, and f is an integer selected from 1, 2 and 3, provided that L and M are not simultaneously O or S;
—$R^{13}$ is hydrogen;
—$R^{14}$ and $R^{15}$ are independently selected from halogen;
-a is an integer selected from 0 or 1;
and when a is 1,
-A is O, CH$_2$, OCH$_2$, CH$_2$O, OCH=CH, C(=O), S(O)$_g$, —CH=CH—, —OC(=O)—; —OC(=O)NH—; —NHC(=O)—; —NHSO$_2$—; and —N=CH—, $NR^{16}$, or N(oxide)$R^{16}$ where $R^{16}$ is as previously described, and g is an integer selected from 0, 1 or 2;
-b is an integer selected from 0, 1, 2, 3, or 4;
and when b is 1 or more,
—$R^5$ and $R^6$ are independently selected from hydrogen, halogen, $(C_1-C_4)$alkyl, cyclo$(C_3-C_6)$alkyl, halo$(C_1-C_4)$alkyl, or aryl;
—B is a cyclic bridging group of the structure;

where,
Q and T are independently selected from —CR$^a$—, —N— and —N(oxide)-, provided that at least one of Q or T is —N—, or —N(oxide)-; and
U is —(CR$^a$R$^b$)$_j$—, where R$^a$ and R$^b$ in Q, T and U are independently selected from hydrogen, hydroxy, $(C_1-C_4)$alkyl, halo$(C_1-C_4)$alkyl, $(C_1-C_4)$alkoxy, $(C_1-C_4)$alkylcarbonyloxy, $(C_1-C_4)$alkylsulfonyl $(C_1-C_4)$alkylphosphinato and $(C_1-C_4)$alkylphosphonato; and j is an integer selected from 1 or 2;
-c is an integer selected from 0, 1, 2, 3 or 4;
and when c is 1 or more,
—$R^7$ and $R^8$ are independently selected from hydrogen, $(C_1-C_4)$alkyl, halo$(C_1-C_4)$alkyl or $(C_1-C_4)$alkoxy, or aryl;
-d is an integer selected from 0 or 1; and,
when d is 1,
-D is selected from O, CH=CH, S(O)$_g$, HC=N, C(=O), OC(=O), C(=O)O, C(=O)NH, $NR^{16}$, N(oxide)$R^{16}$ and $NR^{16}$C(=O) where g and $R^{16}$ are as previously described;
—$R^9$ is selected from $(C_1-C_8)$alkyl; halo$(C_1-C_6)$alkyl; $(C_1-C_4)$alkylthio; $(C_1-C_4)$alkoxy; aryl$(C_1-C_3)$alkyl; aryl$(C_1-C_3)$alkoxy; $(C_2-C_6)$alkenyl; halo$(C_2-C_6)$alkenyl; $(C_2-C_6)$alkynyl; $(C_3-C_7)$cycloalkyl; $(C_4-C_{10})$cycloalkylalkyl; $(C_1-C_3)$alkylamino; di$(C_1-C_3)$alkylamino; aryl$(C_1-C_3)$alkylamino; and phenylamino where phenyl is optionally substituted with one or more of cyano, halogen, $(C_1-C_3)$alkyl, $(C_1-C_3)$alkoxy, halo$(C_1-C_3)$alkyl, or halo$(C_1-C_3)$alkoxy, $(C_1-C_3)$alkyl-S(O)$_g$ where g is previously described, pentahalothio, tri$(C_1-C_3)$alkylsilyl, and; $NR^{16}$ where $R^{16}$ is as previously described;

and

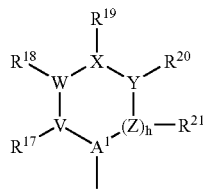

where
h is an integer selected from 0 or 1;
$A^1$ is selected from N, C and C=;
V, W, X, Y and Z are independently selected from O, S, N, N=, C, C= or C(=O);
provided that when V, W, X, Y and Z are selected from N, C or C=, then $R^{17}$ through $R^{21}$, inclusively, are independently selected from hydrogen, halogen, $(C_1-C_6)$alkyl, $(C_2-C_4)$alkenyl, $(C_2-C_4)$alkynyl, halo$(C_1-C_6)$alkyl, hydroxy$(C_1-C_6)$alkyl, cyclo$(C_3-C_6)$alkyl, halo$(C_2-C_4)$alkenyl, halo$(C_2-C_4)$alkynyl, $(C_1-C_6)$alkoxy, $(C_1-C_6)$alkoxy $(C_1-C_6)$alkyl, $(C_2-C_4)$alkenyloxy, $(C_2-C_4)$alkynyloxy, halo $(C_1-C_6)$alkoxy, halo$(C_2-C_4)$alkenyloxy, halo$(C_2-C_4)$alkynyloxy, $(C_1-C_6)$alkylthio, pentahalothio, $(C_1-C_6)$alkylsulfinyl, $(C_1-C_6)$alkylsulfonyl, halo$(C_1-C_6)$alkylthio, halo$(C_1-C_6)$alkylsulfinyl, halo$(C_1-C_6)$alkylsulfonyl, cyano, nitro; $NR^cR^d$, where $R^c$ and $R^d$ are independently selected from hydrogen, $(C_1-C_6)$alkyl, halo$(C_1-C_6)$alkyl, $(C_1-C_6)$alkoxy, $(C_1-C_6)$alkylcarbonyl, and $(C_1-C_6)$alkoxycarbonyl, and where $R^c$ and $R^d$ may be taken together to form a 5- or 6-membered saturated or unsaturated ring containing carbon, O, N, or S; $(C_1-C_6)$alkylcarbonyl, $(C_1-C_6)$alkylcarbonyloxy, $(C_1-C_6)$alkoxycarbonyl, $(C_1-C_6)$alkoxycarbonyloxy, $(C_1-C_6)$alkylaminocarbonyl, $(C_1-C_6)$alkylaminocarbonyloxy, tri$(C_1-C_6)$alkylsilyl, di$(C_1-C_6)$alkylphosphinoyl, aryl, aryloxy, and aryl$(C_1-C_6)$alkoxy;

or
when h is 1; and $A^1$, W and Y are C= and V, X and Z are C; $R^{17}$ and $R^{18}$, or $R^{18}$ and $R^{19}$ may be taken together with —$CR^{22}$=$CR^{23}CR^{24}$=$CR^{25}$—, —$OCR^{22}R^{23}CH_2$—, —$CH_2CR^{22}R^{23}O$—, —$OCR^{22}R^{23}O$—, —$OCR^{22}R^{23}CR^{24}R^{25}O$—, —$OCR^{22}R^{23}CH$=CH—, —$OCR^{22}R^{23}CH_2CH_2$—, —$OCR^{22}$=N—, —N=$CR^{22}O$—, —ON=$CR^{22}$—, —$ONR^{22}C$(=O)—, —$CH_2NR^{22}C$(=O)—, —$C_3H_6$—, —$C_2H_4C$(=O)—, —$SCR^{22}$=N—, —$OCR^{22}R^{23}C$(=O)—, —$CR^{22}$=$CR^{23}NR^{24}$—, —$CR^{22}$=$NNR^{23}$—, —N=$NNR^{22}$— and —N=$CR^{22}N$=N— to form a fused ring, where $R^{22}$ through $R^{25}$, inclusively, are independently selected from hydrogen, halogen, $(C_1-C_3)$alkyl, halo$(C_1-C_3)$alkyl, and aryl;

and agriculturally-acceptable salts thereof.

The present invention also includes compositions containing an insecticidally effective amount of at least one compound of formula I, and optionally, an effective amount of at least one second compound, with at least one insecticidally compatible carrier.

The present invention also includes methods of controlling insects, in an area where control is desired, which comprise applying an insecticidally effective amount of the above composition to the locus of crops, or other areas where insects are present or are expected to be present.

The present invention also includes novel intermediates finding utility in the syntheses of compounds of formula I.

DETAILED DESCRIPTION OF THE INVENTION

The present invention relates to certain new and useful insecticidal and acaricidal compounds, namely substituted phenyl substituted cyclic derivatives (hereinafter termed "compounds of formula I") as depicted in general formula I:

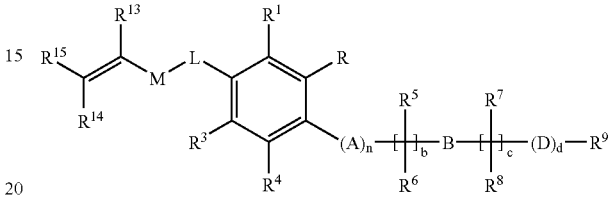

where
—R and $R^4$ are independently selected from hydrogen, halogen, hydroxy, $(C_1-C_6)$alkyl, $(C_3-C_6)$cycloalkyl, $(C_2-C_5)$alkenyl, $(C_2-C_5)$alkynyl, halo$(C_1-C_3)$alkyl, $(C_1-C_3)$alkoxy, halo$(C_1-C_3)$alkoxy, $(C_1-C_3)$alkylthio, halo$(C_1-C_3)$alkylthio, $(C_1-C_3)$alkylsulfonyl, halo$(C_1-C_3)$alkylsulfonyl, cyano, nitro; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=E)-G, and —C($R^{10}$)-J-$R^{11}$, wherein the optional substituent is selected from $(C_1-C_4)$alkyl, halogen, halo$(C_1-C_4)$alkyl, $(C_1-C_4)$alkoxy, $(C_1-C_4)$alkoxy$(C_1-C_4)$alkyl, $(C_3-C_6)$cycloalkyl, $(C_2-C_5)$alkenyl, $(C_2-C_5)$alkynyl, cyano, nitro and aryl;

where
E is selected from O, S, $NR^{12}$, and $NOR^{12}$, where $R^{12}$ is hydrogen, $(C_1-C_4)$alkyl, halo$(C_1-C_4)$alkyl, aryl and aryl$(C_1-C_4)$alkyl;
G is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;
J is selected from O, S, and $NR^{12}$, where $R^{12}$ is as previously described;
$R^{10}$ and $R^{11}$ are independently selected from hydrogen, $(C_1-C_4)$alkyl and halo$(C_1-C_4)$alkyl, and $R^{10}$ and $R^{11}$ may be taken together with —K($CHR^{12}$)$_e$—, where e is an integer of 2 to 4; K is selected from O, S, and $NR^{12}$, where $R^{12}$ is as previously described;
—$R^1$ and $R^3$ are independently selected from hydrogen, halogen and $(C_1-C_3)$alkyl;
-L is selected from selected from $CH_2$, O, S and $NR^{16}$ where $R^{16}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl $(C_1-C_3)$alkyl, halo$(C_2-C_4)$alkenyl$(C_1-C_3)$alkyl, di$(C_1-C_3)$alkylphosphonate, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl;

-M is selected from O, S, *OCH$_2$ and (CH$_2$)$_f$ where the asterisk denotes attachment to L, and f is an integer selected from 1, 2 and 3, provided that L and M are not simultaneously O or S;

—R$^{13}$ is hydrogen;

—R$^{14}$ and R$^{15}$ are independently selected from halogen;

-a is an integer selected from 0 or 1;

and when a is 1,

-A is O, CH$_2$, OCH$_2$, CH$_2$O, OCH=CH, C(=O), S(O)$_g$, —CH=CH—, —OC(=O)—; —OC(=O)NH—; —NHC(=O)—; —NHSO$_2$—; and —N=CH—, NR$^{16}$, or N(oxide)R$^{16}$ where R$^{16}$ is as previously described, and g is an integer selected from 0, 1 or 2;

-b is an integer selected from 0, 1, 2, 3, or 4;

and when b is 1 or more,

—R$^5$ and R$^6$ are independently selected from hydrogen, halogen, (C$_1$-C$_4$)alkyl, cyclo(C$_3$-C$_6$)alkyl, halo(C$_1$-C$_4$)alkyl, or aryl;

—B is a cyclic bridging group of the structure;

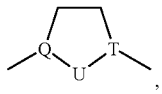

where,

Q and T are independently selected from —CR$^a$—, —N— and —N(oxide)-, provided that at least one of Q or T is —N—, or —N(oxide)-; and U is —(CR$^a$R$^b$)$_j$—, where R$^a$ and R$^b$ in Q, T and U are independently selected from hydrogen, hydroxy, (C$_1$-C$_4$)alkyl, halo(C$_1$-C$_4$)alkyl, (C$_1$-C$_4$)alkoxy, (C$_1$-C$_4$)alkylcarbonyloxy, (C$_1$-C$_4$)alkylsulfonyl (C$_1$-C$_4$)alkylphosphinato and (C$_1$-C$_4$)alkylphosphonato; and j is an integer selected from 1 or 2;

-c is an integer selected from 0, 1, 2, 3 or 4;

and when c is 1 or more,

—R$^7$ and R$^8$ are independently selected from hydrogen, (C$_1$-C$_4$)alkyl, halo(C$_1$-C$_4$)alkyl or (C$_1$-C$_4$)alkoxy, or aryl;

-d is an integer selected from 0 or 1; and, when d is 1,

-D is selected from O, CH=CH, S(O)$_g$, HC=N, C(=O), OC(=O), C(=O)O, C(=O)NH, NR$^6$, N(oxide)R$^{16}$ and NR$^{16}$C(=O) where g and R$^{16}$ are as previously described;

—R$^9$ is selected from (C$_1$-C$_8$)alkyl; halo(C$_1$-C$_6$)alkyl; (C$_1$-C$_4$)alkylthio; (C$_1$-C$_4$)alkoxy; aryl(C$_1$-C$_3$)alkyl; aryl(C$_1$-C$_3$)alkoxy; (C$_2$-C$_6$)alkenyl; halo(C$_2$-C$_6$)alkenyl; (C$_2$-C$_6$)alkynyl; (C$_3$-C$_7$)cycloalkyl; (C$_4$-C$_{10}$)cycloalkylalkyl; (C$_1$-C$_3$)alkylamino; di(C$_1$-C$_3$)alkylamino; aryl(C$_1$-C$_3$)alkylamino; and phenylamino where phenyl is optionally substituted with one or more of cyano, halogen, (C$_1$-C$_3$)alkyl, (C$_1$-C$_3$)alkoxy, halo(C$_1$-C$_3$)alkyl, or halo(C$_1$-C$_3$)alkoxy, (C$_1$-C$_3$)alkyl-S(O)$_g$ where g is previously described, pentahalothio, tri(C$_1$-C$_3$)alkylsilyl, and; NR$^{16}$ where R$^{16}$ is as previously described;

and

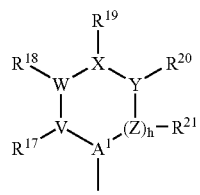

where b is an integer selected from 0 or 1;

A$^1$ is selected from N, C and C=;

V, W, X, Y and Z are independently selected from O, S, N, N=, C, C= or C(=O);

provided that when V, W, X, Y and Z are selected from N, C or C=, then R$^{17}$ through R$^{21}$, inclusively, are independently selected from hydrogen, halogen, (C$_1$-C$_6$)alkyl, (C$_2$-C$_4$)alkenyl, (C$_2$-C$_4$)alkynyl, halo(C$_1$-C$_6$)alkyl, hydroxy(C$_1$-C$_6$)alkyl, cyclo(C$_3$-C$_6$)alkyl, halo(C$_2$-C$_4$)alkenyl, halo(C$_2$-C$_4$)alkynyl, (C$_1$-C$_6$)alkoxy, (C$_1$-C$_6$)alkoxy(C$_1$-C$_6$)alkyl, (C$_2$-C$_4$)alkenyloxy, (C$_2$-C$_4$)alkynyloxy, halo(C$_1$-C$_6$)alkoxy, halo(C$_2$-C$_4$)alkenyloxy, halo(C$_2$-C$_4$)alkynyloxy, (C$_1$-C$_6$)alkylthio, pentahalothio, (C$_1$-C$_6$)alkylsulfinyl, (C$_1$-C$_6$)alkylsulfonyl, halo(C$_1$-C$_6$)alkylthio, halo(C$_1$-C$_6$)alkylsulfinyl, halo(C$_1$-C$_6$)alkylsulfonyl, cyano, nitro; NR$^c$R$^d$, where R$^c$ and R$^d$ are independently selected from hydrogen, (C$_1$-C$_6$)alkyl, halo(C$_1$-C$_6$)alkyl, (C$_1$-C$_6$)alkoxy, (C$_1$-C$_6$)alkylcarbonyl, and (C$_1$-C$_6$)alkoxycarbonyl, and where R$^c$ and R$^d$ may be taken together to form a 5- or 6-membered saturated or unsaturated ring containing carbon, O, N, or S; (C$_1$-C$_6$)alkylcarbonyl, (C$_1$-C$_6$)alkylcarbonyloxy, (C$_1$-C$_6$)alkoxycarbonyl, (C$_1$-C$_6$)alkoxycarbonyloxy, (C$_1$-C$_6$)alkylaminocarbonyl, (C$_1$-C$_6$)alkylaminocarbonyloxy, tri(C$_1$-C$_6$)alkylsilyl, di(C$_1$-C$_6$)alkylphosphinoyl, aryl, aryloxy, and aryl(C$_1$-C$_6$)alkoxy;

or when h is 1; and A$^1$, W and Y are C= and V, X and Z are C; R$^{17}$ and R$^{18}$, or R$^{18}$ and R$^{19}$ may be taken together with —CR$^{22}$=CR$^{23}$CR$^{24}$=CR$^{25}$—, —OCR$^{22}$R$^{23}$CH$_2$—, —CH$_2$CR$^{22}$R$^{23}$O—, —OCR$^{22}$R$^{23}$O—, —OCR$^{22}$R$^{23}$CR$^{24}$R$^{25}$O—, —OCR$^{22}$R$^{23}$CH=CH, —OCR$^{22}$R$^{23}$CH$_2$CH$_2$—, —OCR$^{22}$=N—, —N=CR$^{22}$O—, —ON=CR$^{22}$—, —ONR$^{22}$C(=O)—, —CH$_2$NR$^{22}$C(=O)—, —C$_3$H$_6$—, —C$_2$H$_4$(C=O)—, —SCR$^{22}$=N—, —OCR$^{22}$R$^{23}$C(=O)—, —CR$^{22}$=CR$^{23}$NR$^{24}$—, —CR$^{22}$=NNR$^{23}$—, —N=NNR$^{22}$— and —N=CR$^{22}$N=N— to form a fused ring, where R$^{22}$ through R$^{25}$, inclusively, are independently selected from hydrogen, halogen, (C$_1$-C$_3$)alkyl, halo(C$_1$-C$_3$)alkyl, and aryl;

and agriculturally-acceptable salts thereof.

One skilled in the art will, of course, recognize that within the description set forth above, where V, W, X, Y and Z are independently selected from O, S, N, N=, C, C= or C(=O), that not all of these moieties possess a chemical valence that would allow them to be substituted with a group selected from R$^{17}$ through R$^{21}$. For example, when any one of V, W, X, Y and Z is selected from N=, O, S or C(=O) then the possibility for a substituent on N=, O, S or C(=O) is null. However, the N-oxide of N= may still be formed.

Preferred substituted phenyl substituted cyclic derivatives from the group set forth above are those were R and R⁴ are independently selected from halogen and $(C_1-C_3)$alkyl; L is O; M is $(CH_2)_f$ where f is 1; $R^{13}$ is hydrogen; $R^{14}$ and $R^{15}$ are independently selected from chlorine and bromine; a is an integer selected from 0 or 1, and when a is 1, A is selected from O, $CH_2$ and $OCH_2$; b is an integer selected from 0, 1, 2, 3 or 4, and when b is 1 or more, $R_5$ and $R_6$ are each hydrogen; B is the cyclic bridging group of the structure,

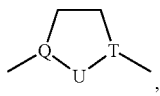

where

Q and T are independently selected from —CR$^a$—, and —N—, where R$^a$ is hydrogen or hydroxy; provided that at least one of Q and T is —N— and U is —(CR$^a$R$^b$)$_j$—, where R$^a$ and R$^b$ are hydrogen, and j is 2;

c is an integer selected from 0, 1, 2, 3 or 4, and when c is 1 or more, R⁷ and R⁸ are hydrogen; d is an integer selected from 0 or 1, and when d is 1, D is selected from C(=O), C(=O)NH and S(O)$_g$ where g is 2;

R⁹ is selected from $(C_1-C_8)$alkyl, and

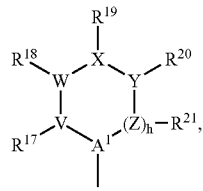

where h is 1, and i) A¹, W and Y are C= and V, X and Z are C, or ii) A¹, W and Y are C=, V is N and X and Z are C; R¹⁷ through R²¹, inclusively, are independently selected from hydrogen, halogen, $(C_1-C_6)$alkyl and halo$(C_1-C_3)$alkyl; and when i) A¹, W and Y are C= and V, X and Z are C, R¹⁷ and R¹⁸ or R¹⁸ and R¹⁹ may be taken together with —OCR²²R²³CH₂— or —CH₂CR²²R²³O— to form a fused ring, where R²² and R²³ are each hydrogen, fluorine or $(C_1-C_3)$alkyl.

More preferred phenyl substituted cyclic derivatives of the group set forth above are those where R and R⁴ are each chlorine; R¹ and R³ are each hydrogen; a is an integer selected from 0 or 1, and when a is 1, A is O or OCH₂, b is an integer selected from 0 or 1; j is 2, Q is CR$^a$ or N, where R$^a$ is hydrogen, and T is N; c is an integer selected from 0 or 1; d is 0 or 1, and when d is 1, D is C(=O), or S(O)$_g$; h is 1, and i) A¹, W and Y are C= and V, X and Z are C; or ii) A¹, W and Y are C=, V is N, and X and Z are C; and yet more preferred are those where a is an integer selected from 0 or 1, and when a is 1, A is OCH₂; c is 0; d is an integer selected from 0 or 1, and when d is 1, D is S(O)$_g$; R²¹ is hydrogen; and R¹⁷ through R²⁰, inclusively, are independently selected from hydrogen, chlorine and trifluoromethyl.

More specifically, the new and useful insecticidal and acaricidal substituted phenyl substituted cyclic derivatives of formula I are as shown below:

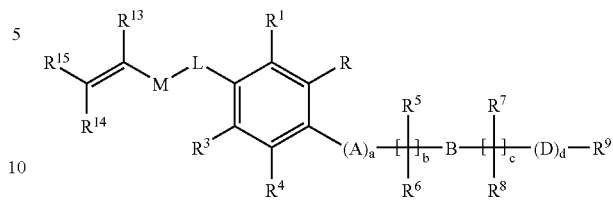

I where

—R and R⁴ are independently selected from hydrogen, halogen or $(C_1-C_3)$alkyl;

—R¹ and R³ are hydrogen;

L is O; M is $(CH_2)_f$ where f is 1; R¹³ is hydrogen; and R¹⁴ and R¹⁵ are each chlorine;

-a is an integer selected from 0 or 1;

and when a is 1,

-A is selected from O, CH₂ or OCH₂;

-b is an integer selected from 0, 1, 2, 3 or 4;

and when b is 1 or more,

—R⁵ and R⁶ are each hydrogen;

—B is a cyclic bridging group of the structure,

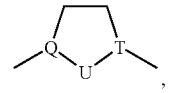

where

Q and T are independently selected from —CR$^a$—, —N— and —N(oxide)-, provided that at least one of Q or T is —N— or —N(oxide)-; where R$^a$ is hydrogen or hydroxy; U is —(CR$^a$R$^b$)$_j$—, where R$^a$ and R$^b$ are hydrogen and j is an integer selected from 1 or 2;

-c is an integer selected from 0, 1, 2, 3 or 4;

and when c is 1 or more,

—R⁷ and R⁸ are hydrogen;

-d is an integer selected from 0 or 1;

and when d is 1,

-D is selected from O, C(=O), C(=O)NH and S(O)$_g$ where g is 2;

—R⁹ is selected from $(C_1-C_8)$alkyl, and

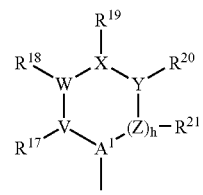

where

-h is 1;

A¹ is selected from N, C and C=;

V, W, X, Y and Z are independently selected from O, S, N, N=, C, C=O or C(=O); provided that when V, W, X, Y and Z are selected from N, C or C=, then R¹⁷ through R²¹, inclusively, are independently selected from hydrogen, halogen, $(C_1-C_6)$alkyl and halo$(C_1-C_3)$alkyl;

or when

A$^1$, W and Y are C═ and V, X and Z are C; R$^{17}$ and R$^{18}$, or R$^{18}$ and R$^{19}$ may be taken together with —OCR$^{22}$R$^{23}$CH$_2$—, where R$^{22}$ and R$^{23}$ independently selected from hydrogen or (C$_1$-C$_3$)alkyl;

and agriculturally acceptable salts thereof.

Preferred of the more specific substituted phenyl substituted cyclic derivatives from the group set forth above are those were R and R$^4$ are each chlorine; a is an integer selected from 0 or 1, and when a is 1, A is O or OCH$_2$, b is an integer selected from 0 or 1; j is 2, Q is CR$^a$ or N, where R$^a$ is hydrogen, and T is N; c is an integer selected from 0 or 1; d is 0 or 1, and when d is 1, D is C(═O), or S(O)$_g$; h is 1, and i) A$^1$, W and Y are C═ and V, X and Z are C; or ii) A$^1$, W and Y are C═, V is N, and X and Z are C; and more preferred are whose where a is an integer selected from 0 or 1, and when a is 1, A is OCH$_2$; c is 0; d is an integer selected from 0 or 1, and when d is 1, D is S(O)$_g$; R$^{21}$ is hydrogen; and R$^{17}$ through R$^{20}$, inclusively, are independently selected from hydrogen, chlorine and trifluoromethyl.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention comprise causing an insecticidally effective amount of a compound of formula I to be administered to insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which are referred to as pro-insecticides.

Another aspect of the present invention relates to compositions containing an insecticidally effective amount of at least one compound of formula I.

Another aspect of the present invention relates to compositions containing an insecticidally effective amount of at least one compound of formula I, and an effective amount of at least one second compound.

Another aspect of the present invention relates to methods of controlling insects by applying an insecticidally effective amount of a composition as set forth above to a locus of crops such as, without limitation, cereals, cotton, vegetables, and fruits, or other areas where insects are present or are expected to be present.

Another aspect of the present invention relates to novel intermediates finding utility in the syntheses of compounds of formula I.

The present invention also includes the use of the compounds and compositions set forth herein for control of non-agricultural insect species, for example, dry wood termites and subterranean termites; as well as for use as pharmaceutical agents. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having six to ten carbon atoms, for example, phenyl or naphthyl. The term "heteroaryl" refers to an aromatic ring structure, including fused rings, in which at least one of the atoms is other than carbon, for example, without limitation, sulfur, oxygen, or nitrogen. The term "GC analysis" refers to gas chromatographic analysis of; while the term "TLC analysis" refers to thin layer chromatographic analysis of, for example a reaction mixture. The term "HPLC" refers to high pressure liquid chromatography, as it relates to, for example a method of separating components from a reaction mixture. The term "DMF" refers to N,N-dimethylformamide. The term "THF" refers to tetrahydrofuran. The term "DBU" refers to 1,8-diazabicyclo[5.4.0]undec-7-ene. The term "DEAD" refers to diethyl azodicarboxylate. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one of a second compound, or with at least one compatible carrier, which causes the destruction or the inhibition of action of insects or acarids. The term "independently selected from" as set forth above and in the claims section of the present specification refers to the possibility that moieties, for example the R$^{14}$ and R$^{15}$, may be the same or they may be different within the group that the selection is made.

The phenyl substituted cyclic derivatives of formula I can be synthesized by methods that are individually known to one skilled in the art from available intermediate compounds.

Scheme 1 below illustrates a general procedure for synthesizing phenyl substituted cyclic derivatives of formula I, inter alia, where, for example, R$^1$ and R$^3$ are hydrogen; R and R$^4$ are each chlorine; R$^2$ is -L-M-C(R$^{13}$)═C(R$^{14}$)(R$^{15}$), and L is O, M is CH$_2$, R$^{13}$ is hydrogen, and R$^{14}$ and R$^{15}$ are each chlorine; a is 1 and A is OCH$_2$; b and c are 0; d is 1 and D is C(═O)O; Q is CR$^a$ where R$^a$ is hydrogen; T is N, U is (CR$^a$R$^b$)$_j$ where j is 2; and, for example, R$^9$ is (C$_1$-C$_8$)alkyl:

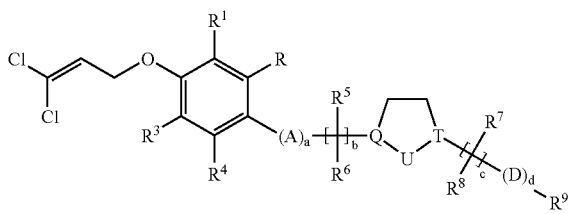

Scheme 1

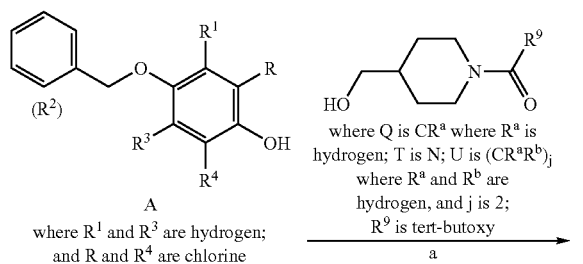

A
where $R^1$ and $R^3$ are hydrogen; and R and $R^4$ are chlorine where Q is $CR^a$ where $R^a$ is hydrogen; T is N; U is $(CR^aR^b)_j$ where $R^a$ and $R^b$ are hydrogen, and j is 2; $R^9$ is tert-butoxy

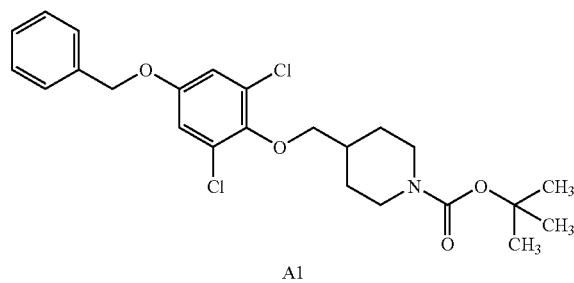

A1
where a is 1 and A is $OCH_2$; b and c are 0, d is 1 and D is C(=O)O

A1 →(b)

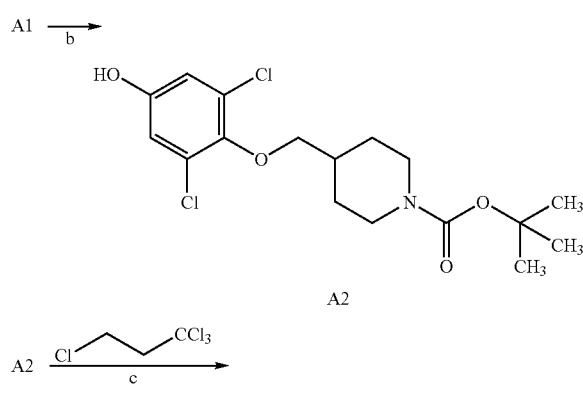

A2

A2 →(c) with $Cl$—$CCl_3$

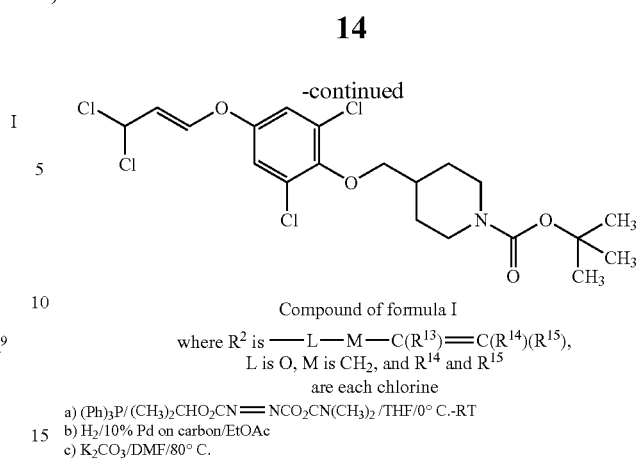

Compound of formula I
where $R^2$ is —L—M—C($R^{13}$)=C($R^{14}$)($R^{15}$),
L is O, M is $CH_2$, and $R^{14}$ and $R^{15}$ are each chlorine a) $(Ph)_3P/(CH_3)_2CHO_2CN=NCO_2CN(CH_3)_2$/THF/0° C.-RT
b) $H_2$/10% Pd on carbon/EtOAc
c) $K_2CO_3$/DMF/80° C.

As depicted in Scheme 1, an appropriately substituted hydroxy compound, for example, the commercially available tert-butyl 4-(hydroxymethyl)piperidinecarboxylate was coupled with a phenol (A), for example the known compound 2,6-dichloro-4-(phenylmethoxy)phenol, affording the corresponding tert-butyl 4-{[2,6-dichloro-4-(phenylmethoxy)phenoxy]methyl}piperidinecarboxylate (A1). The intermediate (A1) was in turn treated with hydrogen gas under catalytic conditions using, for example, a Parr hydrogenation apparatus, to convert the phenylmethoxy moiety of (A1) to a hydroxy moiety, thereby making the hydroxy moiety available for further reaction. The so-prepared hydroxy derivative (A2) was then reacted with an appropriate haloalkane, for example, 1,1,1,3-tetrachloropropane, under basic conditions, yielding the corresponding dihaloalkene derivative, a compound of formula I, for example, tert-butyl 4-{[4-(3,3-dichloroprop-2-enyloxy)-2,6-dichlorophenoxy]methyl}piperidinecarboxylate. Example 1, set forth below, provides detailed methods to how compounds of formula I shown in Scheme 1 were prepared.

Scheme 2 below illustrates a general procedure for synthesizing phenyl substituted cyclic derivatives of formula I, inter alia, where, for example, where $R^1$ and $R^3$ are hydrogen; R and $R^4$ are chlorine, $R^2$ is -L-M-C($R^{13}$)=C($R^{14}$)($R^{15}$), and L is O, M is $CH_2$, $R^{13}$ is hydrogen, and $R^{14}$ and $R^{15}$ are each chlorine; a, b, c and d are 0; U is $(CR^aR^b)j$ where $R^a$ and $R^b$ are hydrogen and j is 2; and $R^9$ is

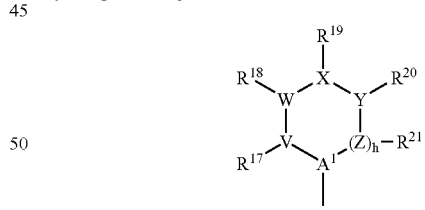

where h is 1; $A^1$, W and Y are C=; V, X and Z are C; and $R^{20}$ and $R^{21}$ are hydrogen:

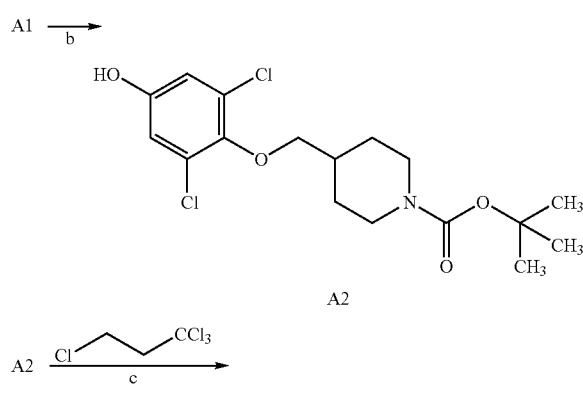

Scheme 2

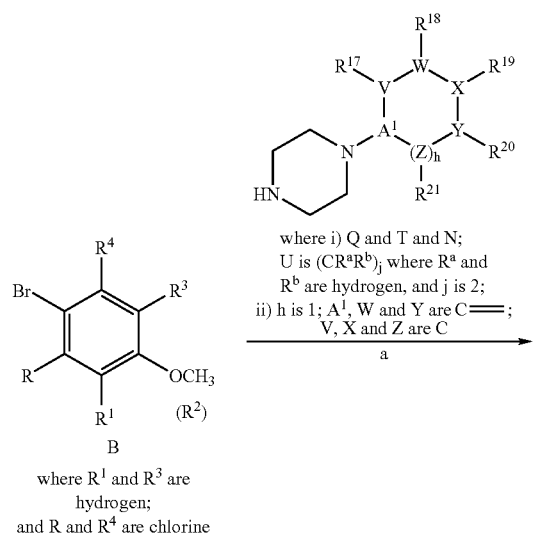

where $R^1$ and $R^3$ are hydrogen;
and R and $R^4$ are chlorine

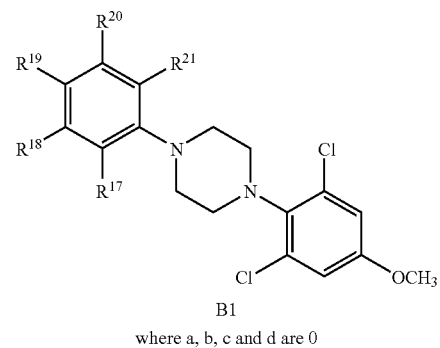
where a, b, c and d are 0

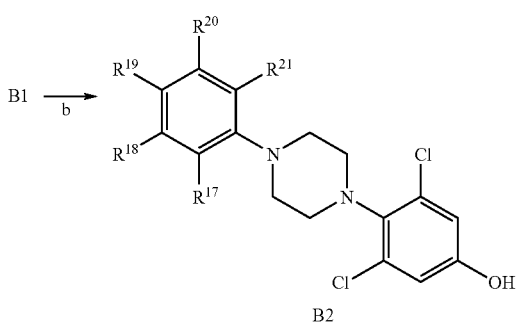

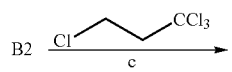

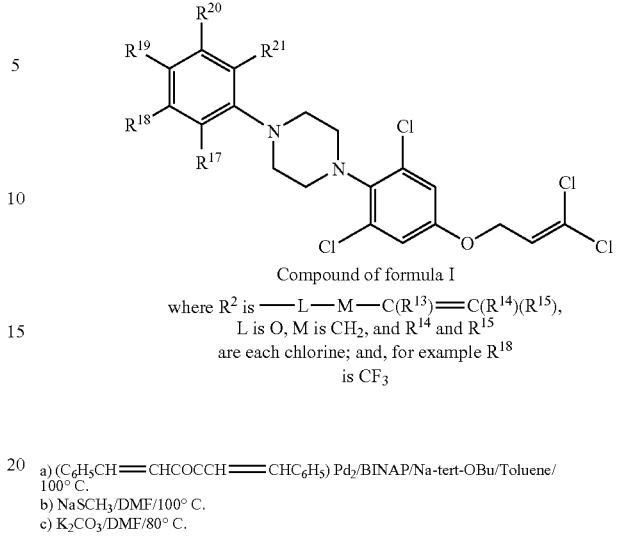

Compound of formula I
where $R^2$ is —L—M—C($R^{13}$)=C($R^{14}$)($R^{15}$),
L is O, M is $CH_2$, and $R^{14}$ and $R^{15}$
are each chlorine; and, for example $R^{18}$
is $CF_3$ a) ($C_6H_5CH$=CHCOCCH=CH$C_6H_5$) $Pd_2$/BINAP/Na-tert-OBu/Toluene/100° C.
b) $NaSCH_3$/DMF/100° C.
c) $K_2CO_3$/DMF/80° C.

As depicted in Scheme 2, an appropriately substituted alkoxybenzene (B), for example, the known compound 1,3-dichloro-5-methoxy-2-bromobenzene, was reacted with the commercially available α,α,α-trifluoro-meta-tolylpiperazine in the presence of at least one catalyst, for example, tris(dibenzylideneacetone)dipalladium(0) and racemic-2,2'-bis(diphenylphosphono)-1,1'-binaphthyl (BINAP), under strong basic conditions, to afford the corresponding coupled derivative, 1,3-dichloro-5-methoxy-2-{4-[4-(trifluoromethyl)phenyl]piperazinyl}benzene (B1). Intermediate (B1) was then dealkylated with, for example, sodium methanethiolate, to yield the corresponding phenol, 3,5-dichloro-4-{4-[4-(trifluoromethyl)phenyl]piperazinyl}phenol (B2). Intermediate (B1) was then reacted under basic conditions with, for example, an appropriate haloalkene, such as 1,1,3-trichloropropene, in a manner analogous to that set forth in Scheme 1, yielding a compound of formula I, for example 5-(3,3-Dichloroprop-2-enyloxy)-1,3-dichloro-2-{4-[3-(trifluoromethyl)phenyl]piperazinyl}benzene. Example 2, set forth below, provides detailed methods to how compounds of formula I shown in Scheme 2 were prepared.

Scheme 3 below illustrates a general procedure for synthesizing phenyl substituted cyclic derivatives of formula I similar to those depicted in Scheme 2, except that a is 1, and A is $OCH_2$ and b is 1, and $R^5$ and $R^6$ are each hydrogen:

Scheme 3

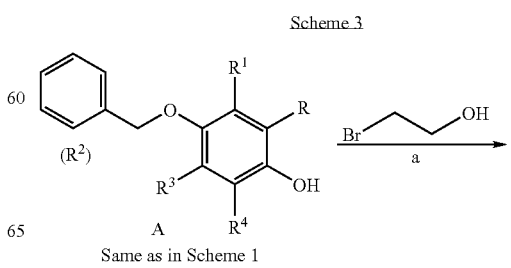

Same as in Scheme 1

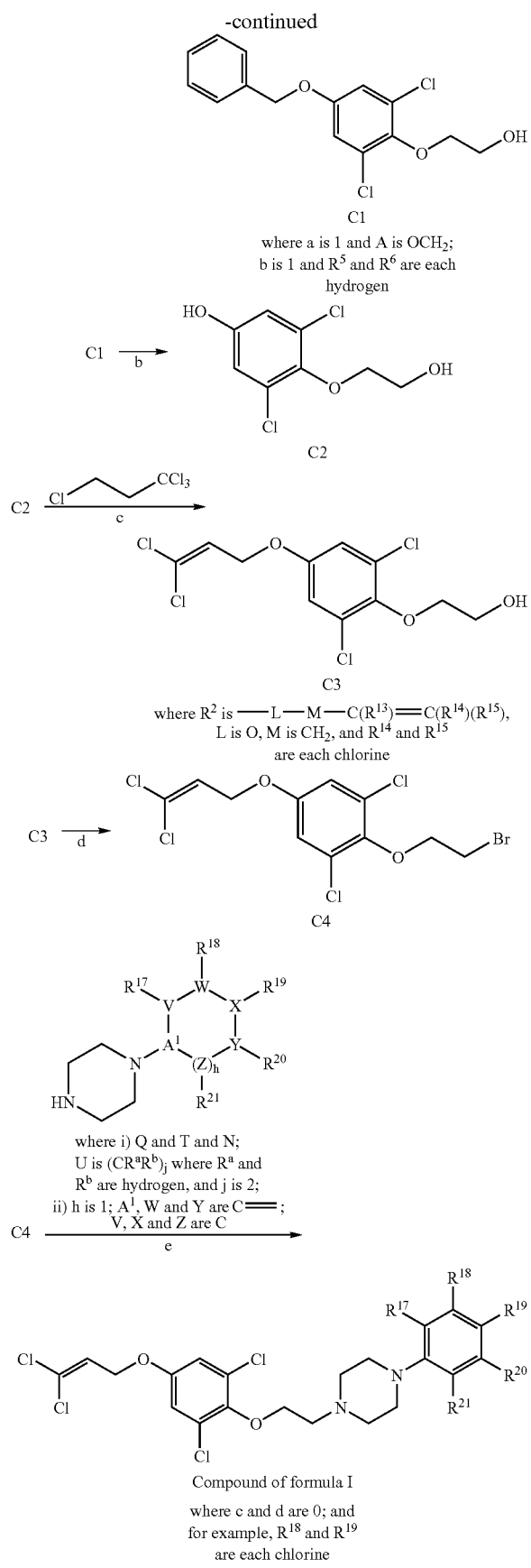
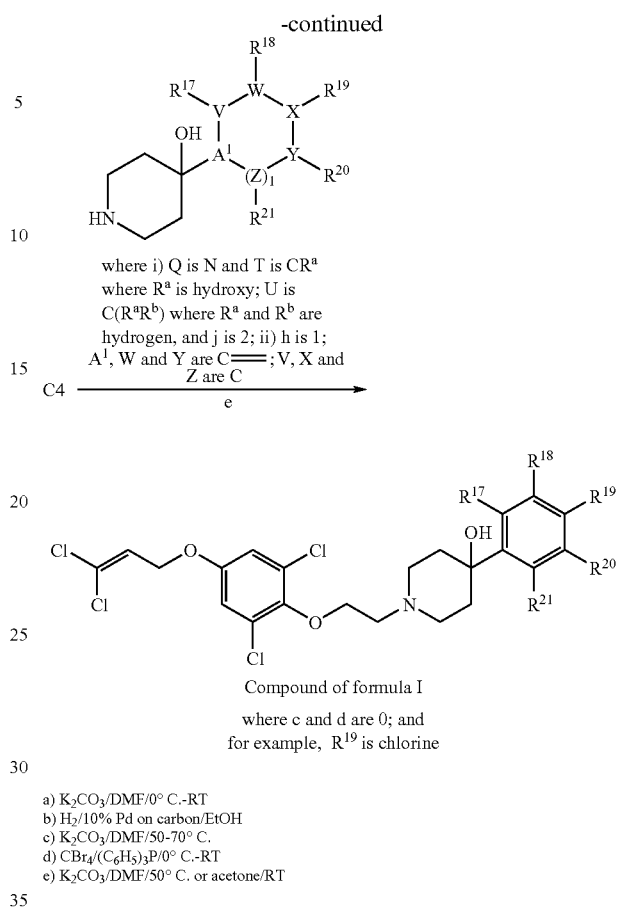

a) $K_2CO_3$/DMF/0° C.-RT
b) $H_2$/10% Pd on carbon/EtOH
c) $K_2CO_3$/DMF/50-70° C.
d) $CBr_4$/$(C_6H_5)_3$P/0° C.-RT
e) $K_2CO_3$/DMF/50° C. or acetone/RT As depicted in Scheme 3, an appropriately substituted phenol (A), for example the known compound 2,6-dichloro-4-(phenylmethoxy)phenol, was reacted with an appropriate halide, for example 2-bromoethan-1-ol, under basic conditions, providing the corresponding alcohol, for example 2-[2,6-dichloro-4-(phenylmethoxy)phenoxy]ethan-1-ol (C1). Intermediate (C1) was in turn treated with hydrogen gas under catalytic conditions in the manner set forth in Scheme 1, which converted the phenylmethoxy moiety of (C1) to a hydroxy moiety, thereby making the hydroxy moiety available for further reaction. The so-prepared hydroxy derivative (C2) was then reacted with an appropriate haloalkane, for example, 1,1,1,3-tetrachloropropane, under basic conditions, yielding the corresponding dihaloalkene derivative (C3), for example 2-[4-(3,3-dichloroprop-2-enyloxy)-2,6-dichlorophenoxy]ethan-1-ol. Intermediate (C3) was then brominated with, for example carbon tetrabromide, providing intermediate (C4); which was in turn reacted with, for example the commercially available (3,4-dichlorophenyl)piperazine, yielding the corresponding compound of formula I. Examples 3 and 7, set forth below, provide detailed methods to how compounds of formula I shown in Scheme 3 were prepared.

Scheme 4 below illustrates a general procedure for synthesizing phenyl substituted cyclic derivatives of formula I similar to those depicted in Scheme 2, except that d is 1, and D is C(=O) or $S(O)_g$ where g is 2:

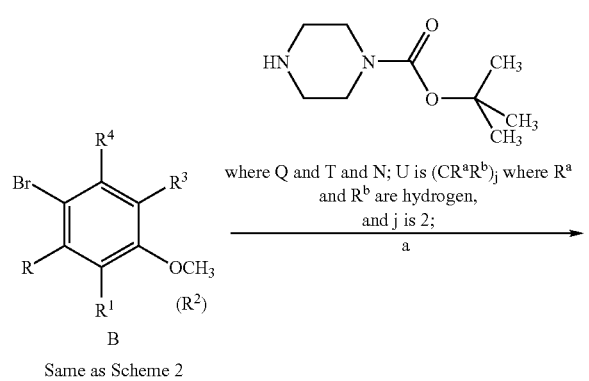

a) ($C_6H_5CH$═$CHCOCCH$═$CHC_6H_5$) $Pd_2$/BINAP/Na-tert-OBu/Toluene/ 100° C.
b) $NaSCH_3$/ DMF/100° C.
c) $K_2CO_3$/DMF/80° C.
d) $AlCl_3$/$CH_2Cl_2$/0° C.-RT
e) DBU/$CH_3CN$/80° C.

As depicted in Scheme 4, intermediate (D3), for example 4-[4-(3,3-dichloroprop-2-enyloxy)-2,6-dichlorophenyl]piperazinecarboxylate, was prepared from the known compound 1,3-dichloro-5-methoxy-2-bromobenzene (B) in a manner analogous to that discussed above for the preparation of a compound of formula I, as depicted in Scheme 2. Intermediate (D3) was, however, reacted further to obtain other compounds of formula I. For example, intermediate (D3) was treated with aluminum chloride in an appropriate solvent to cleave the tert-butyl ester portion from the molecule, thereby providing the free piperazine intermediate (D4), which was in turn reacted with an appropriate halide, for example 4-trifluoromethylbenzoyl chloride, affording the corresponding compound of formula I, 4-[4-(3,3-dichloroprop-2-enyloxy)-2,6-dichlorophenyl]piperazinyl 4 (trifluoromethyl)phenyl ketone. Examples 4 and 5, set forth below, provide detailed methods to how compounds of formula I shown in Scheme 4 were prepared.

Scheme 5 below illustrates a general procedure for synthesizing phenyl substituted cyclic derivatives of formula I, inter alia, where, for example, $R^1$ and $R^3$ are hydrogen; R and $R^4$ are each chlorine; $R^2$ is -L-M-$C(R^{13})$═$C(R^{14})(R^{15})$, and L is O, M is $CH_2$, $R^{13}$ is hydrogen, and $R^{14}$ and $R^{15}$ are each chlorine; a is 1 and A is $OCH_2$; b, c and d are 0; Q is $CR^a$ where $R^a$ is hydrogen and T is N; U is $(CR^aR^b)_j$ where j is 2, and $R^a$ and $R^b$ are hydrogen; and $R^9$ is the same as depicted in Scheme 2, where h is 1; $A^1$, W and Y are C═; V is N; X and Z are C; and $R^{17}$, $R^{18}$, $R^{20}$ and $R^{21}$ are hydrogen:

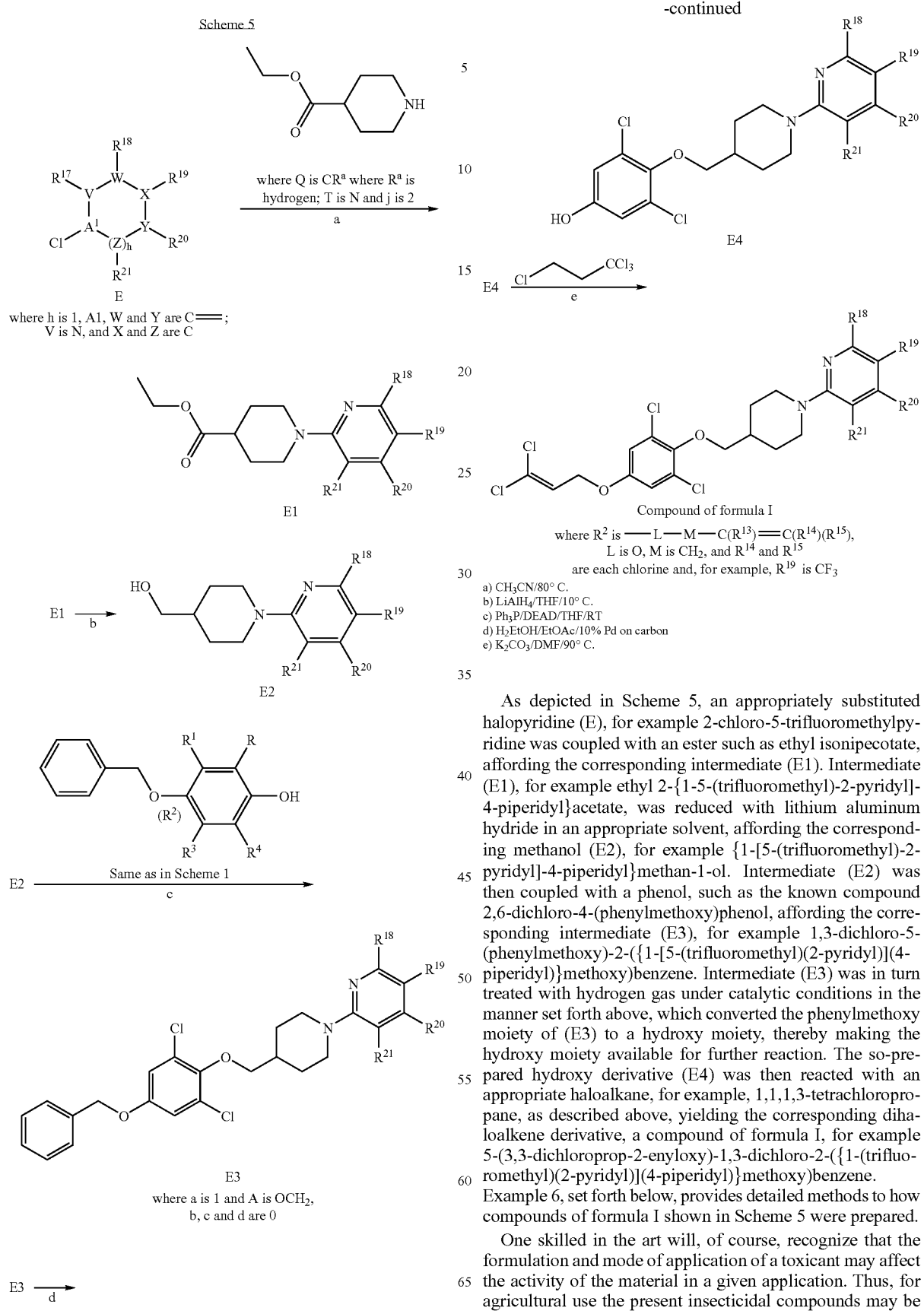

As depicted in Scheme 5, an appropriately substituted halopyridine (E), for example 2-chloro-5-trifluoromethylpyridine was coupled with an ester such as ethyl isonipecotate, affording the corresponding intermediate (E1). Intermediate (E1), for example ethyl 2-{1-5-(trifluoromethyl)-2-pyridyl]-4-piperidyl}acetate, was reduced with lithium aluminum hydride in an appropriate solvent, affording the corresponding methanol (E2), for example {1-[5-(trifluoromethyl)-2-pyridyl]-4-piperidyl}methan-1-ol. Intermediate (E2) was then coupled with a phenol, such as the known compound 2,6-dichloro-4-(phenylmethoxy)phenol, affording the corresponding intermediate (E3), for example 1,3-dichloro-5-(phenylmethoxy)-2-({1-[5-(trifluoromethyl)(2-pyridyl)](4-piperidyl)}methoxy)benzene. Intermediate (E3) was in turn treated with hydrogen gas under catalytic conditions in the manner set forth above, which converted the phenylmethoxy moiety of (E3) to a hydroxy moiety, thereby making the hydroxy moiety available for further reaction. The so-prepared hydroxy derivative (E4) was then reacted with an appropriate haloalkane, for example, 1,1,1,3-tetrachloropropane, as described above, yielding the corresponding dihaloalkene derivative, a compound of formula I, for example 5-(3,3-dichloroprop-2-enyloxy)-1,3-dichloro-2-({1-(trifluoromethyl)(2-pyridyl)](4-piperidyl)}methoxy)benzene.

Example 6, set forth below, provides detailed methods to how compounds of formula I shown in Scheme 5 were prepared.

One skilled in the art will, of course, recognize that the formulation and mode of application of a toxicant may affect the activity of the material in a given application. Thus, for agricultural use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4-chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sufonyl]methyl]benzoic acid ("bensulfuron"), 2-[[[[(4,6-dimethoxy-2-pyrimidinyl)amino]carbonyl]amino]sulfonyl]-1-methy-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]benzenesulfonamide ("triasulfuron"); 2-(4-aryloxyphenoxy)alkanoic acids such as (+/−)-2[4-[(6-chloro-2-benzoxazolyl)oxy]phenoxy]-propanoic acid (fenoxaprop"), (+/−)-2-[4[[5-(trifluoromethyl)-2-pyridinyl]oxy]-phenoxy] propanoic acid ("fluazifop"), (+/−)-2-[4-(6chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide, ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, bifenthrin, cypermethrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with one or more of second compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldicarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudoinonas, azotobacter, azospirillum, rhizobiwn*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates one protocol for the preparation of tert-butyl 4-{[4-(3,3-dichloroprop-2-enyloxy)-2,6-dichlorophenoxy]methyl}piperidinecarboxylate (Compound 4 in table below)

Step A Synthesis of tert-butyl 4-{[2,6-dichloro-4-(phenylmethoxy)phenoxy]methyl}piperidinecarboxylate as an intermediater A stirred solution of 10.0 grams (0.046 mole) of tert-butyl 4-(hydroxymethyl)piperidinecarboxylate (commercially available) and 12.5 grams (0.046 mole) of 2,6-dichloro-4-(phenylmethoxy)phenol (known compound) in 100 mL of THF was cooled in an ice-water bath and 12.2 grams (0.046 mole) of triphenylphosphine was added in one portion. Upon completion of addition 9 mL (0.046 mole) of diisopropyl azodicarboxylate was added dropwise during a five minute period. Upon completion of addition the reaction mixture was allowed to warm to ambient temperature where it stirred during an 18 hour period. After this time the reaction mixture was concentrated under reduced pressure to a residue. The residue was purified with column chromatography on silica gel using methylene chloride as an eluant. The appropriate fractions were combined and concentrated under reduced pressure, yielding 21 grams of the subject compound. The NMR spectrum was consistent with the proposed structure.

Step B Synthesis of tert-butyl 4-[(2,6-dichloro-4-(hydroxyphenoxy)methyl]piperidinecarboxylate as an Intermediater A solution of 21.0 grams (0.045 mole) of tert-butyl 4-{[2,6-dichloro-4-(phenylmethoxy)phenoxy]methyl}piperidinecarboxylate in 500 mL of ethyl acetate was treated with hydrogen gas in the presence of a catalytic amount of 10% palladium on carbon using a Parr hydrogenaton apparatus. Following the completion of the reaction, the reaction mixture was filtered and the filtrate was concentrated under reduced pressure to a residue. The yield of the subject compound was 16.8 grams. The NMR spectrum was consistent with the proposed structure.

Step C Synthesis of Compound 4

A solution of 16.8 grams (0.045 mole) of tert-butyl 4-[(2,6-dichloro-4-(hydroxyphenoxy)methyl]piperidinecarboxylate in 100 mL of DMF was stirred and 12.4 grams (0.068 mole) of 1,1,1,3-tetrachloropropane was added, followed by 12.4 grams (0.090 mole) of potassium carbonate, wherein both reactants were added in single portions. Upon completion of addition the reaction mixture was warmed to 80° C. where it stirred during an 18 hour period. After this time the reaction mixture was cooled, diluted with 250 mL of water and extracted with three 100 mL portions of diethyl ether. The combined extracts were dried with sodium sulfate, filtered, and the filtrate concentrated under reduced pressure to a residue. The residue was purified with column chromatography on silica gel using methylene chloride as an eluant. The appropriate fractions were combined and concentrated under reduced pressure, yielding 14 grams of Compound 4. The NMR spectrum was consistent with the proposed structure.

EXAMPLE 2

This example illustrates one protocol for the preparation of 5-(3,3-Dichloroprop-2-enyloxy)-1,3-dichloro-2-{4-[3-(trifluoromethyl)phenyl]piperazinyl}benzene (Compound 11 in table below)

Step A Synthesis of 1,3-dichloro-5-methoxy-2-{4-[3-(trifluoromethyl)phenyl]piperazinyl}benzene as an Intermediate A stirred mixture of 2.5 grams (0.0096 mole) of 1,3-dichloro-5-methoxy-2-bromobenzene (known compound), 0.18 mL (0.0096 mole) of 1-(α,α,α-trifluoro-meta-tolyl)piperazine (known compound), 0.18 gram (0.0002 mole) of tris(dibenzylideneacetone)dipalladium(0), 0.36 gram (0.0006 mole) of racemic-2,2'-bis(diphenylphosphono)-1,1'-binaphthyl, and 1.66 grams (0.017 mole) of sodium tert-butoxide in 100 mL of toluene was heated at 100° C. for about 60 hours. After this time, the reaction mixture was cooled and washed with two 10 mL portions of water. The organic layer was dried with sodium sulfate, filtered, and concentrated under reduced pressure to a residue. The residue was purified with column chromatography on silica gel using 1:3 and 1:1 mixtures of methylene chloride:hexane as eluants. The appropriate fractions were combined and concentrated under reduced pressure, yielding 2.1 grams of the subject compound, mp 87-89° C. The NMR spectrum was consistent with the proposed structure.

Step B Synthesis of 3,5-dichloro-4-{4-[3-(trifluoromethyl)phenyl]piperazinyl}phenol as an Intermediate A suspension of 0.8 gram (0.011 mole) of sodium methanethiolate in 25 mL of DMF was stirred, and a solution of 1.8 grams (0.0044 mole) of 1,3-dichloro-5-methoxy-2-{4-[3-(trifluoromethyl)phenyl]piperazinyl}benzene in 40 mL of DMF was added. Upon completion of addition, the reaction mixture was heated to 100° C. where it stirred for two hours. After this time, the reaction mixture was cooled in an ice-water bath and 50 mL of water, followed by 25 mL of an aqueous solution of 10% hydrochloric acid, were added dropwise. The reaction mixture was then saturated with sodium chloride and extracted with two 50 mL portions of diethyl ether. The combined extracts were dried with sodium sulfate, filtered, and concentrated under reduced pressure to a residue. The residue was purified with column chromatography on silica gel using 1:1 methylene chloride:hexane, then 100% methylene chloride as eluants. The appropriate fractions were combined and concentrated under reduced pressure, yielding 1.1 grams of the subject compound. The NMR spectrum was consistent with the proposed structure.

Step C Synthesis of Compound 11

This compound was prepared in a manner analogous to that of Example 1 Step C, by the reaction of 0.25 gram (0.00064 mole) of 3,5-dichloro-4-{4-[3-(trifluoromethyl)phenyl]piperazinyl}phenol, 0.18 gram (0.0012 mole) of 1,1,1,3-tetrachloropropane and 0.13 gram (0.00096 mole) of potassium carbonate in 8 mL of DMF. The crude reaction product was purified with column chromatography on silica gel using 1:3 methylene chloride:hexane as an eluant. The appropriate fractions were combined and concentrated under reduced pressure, yielding 0.1 gram of Compound 11 The NMR spectrum was consistent with the proposed structure.

EXAMPLE 3

This example illustrates one protocol for the preparation of 2-{2-[3,4-dichlorophenyl)piperazinyl]ethoxy}-5-(3,3-dichloroprop-2-enyloxy)-1,3-dichlorobenzene (Compound 20 in table below)

Step A Synthesis of 2-[2,6-dichloro-4-(phenylmethoxy)phenoxy]ethan-1-ol as an Intermediate A stirred solution of 15.0 grams (0.056 mole) of 2,6-dichloro-4-(phenylmethoxy)phenol (known compound) and 15.0 grams (0.109 mole) of potassium carbonate in 200 mL of DMF was cooled to 0-4° C. and 8.4 grams (0.067 mole) of 2-bromoethan-1-ol was slowly added. Upon completion of addition the reaction mixture was allowed to warm to ambient temperature where it was stirred during an 18 hour period. After this time water was added to the reaction mixture, and the mixture was extracted with two 150 mL portions of diethyl ether. The combined extracts were dried with sodium sulfate, filtered, and the filtrate was concentrated under reduced pressure to yield 17.1 grams of residual oil. The NMR spectrum was consistent with the proposed structure.

Step B Synthesis of 3,5-dichloro-4-(2-hydroxyethoxy)phenol as an Intermediate

This compound was prepared in a manner analogous to that of Example 1 Step B, by the treatment of 16.0 grams (0.051 mole) of 2-[2,6-dichloro-4-(phenylmethoxy)phenoxy]ethan-1-ol with hydrogen gas in the presence of a catalytic amount of 10% palladium on carbon in about 400 mL of ethanol using a Parr hydrigenaton apparatus. Following the theoretical uptake of hydrogen, the reaction mixture was filtered. The filtrate was concentrated under reduced pressure to a residue. The residue was purified with column chromatography on silica gel using 1:2 ethyl acetate:hexane as an eluant. The appropriate fractions were combined and concentrated under reduced pressure, yielding 10.5 grams of the subject compound. The NMR spectrum was consistent with the proposed structure.

Step C Synthesis of 2-[4-(3,3-dichloroprop-2-enyloxy)-2,6-dichlorophenoxy]ethan-1-ol as an Intermediate This compound was prepared in a manner analogous to that of Example 1 Step C, by the reaction of 10.0 grams (0.045 mole) of 3,5-dichloro-4-(2-hydroxyethoxy)phenol, 12.0 grams (0.066 mole) of 1,1,1,3-tetrachloropropane and 12.0 grams (0.086 mole) of potassium carbonate in 100 mL of DMF. The reaction mixture was warmed to 50° C. where it stirred during an 18 hour period, then it was warmed to 70° C. where it stirred during an additional five hour period. After this time the reaction mixture was cooled, water was added, and the mixture was extracted with two 150 mL portions of diethyl ether. The combined extracts were washed with an aqueous solution saturated with sodium chloride, dried with sodium sulfate and filtered. The filtrate was concentrated under reduced pressure to a residue. The residue was purified with column chromatography on silica gel using 1:4 ethyl acetate:hexane as an eluant. The appropriate fractions were combined and concentrated under reduced pressure, yielding 10.9 grams of the subject compound. The NMR spectrum was consistent with the proposed structure.

Step D Synthesis of 1-[4-(3,3-dichloroprop-2-enyloxy)-2,6-dichlorophenoxy]-2-bromoethane as an Intermediate A stirred solution of 2.5 grams (0.0075 mole) of 2-[4-(3,3-dichloroprop-2-enyloxy)-2,6-dichlorophenoxy]ethan-1-ol and 3.1 grams (0.0094 mole) of carbon tetrabromide in 150 mL of methylene chloride was cooled to 0-4° C. and 6.0 grams (0.0152 mole) of triphenylphosphine was added portion-wise. Upon completion of addition the reaction mixture was allowed to warm to ambient temperature where it stirred during an 18 hour period. After this time the reaction mixture was concentrated under reduced pressure to a residue. The residue was purified with column chromatography on silica gel using 1:5 ethyl acetate:hexane as an eluant. The appropriate fractions were combined and concentrated under reduced pressure, yielding 2.7 grams of the subject compound. The NMR spectrum was consistent with the proposed structure.

Step E Synthesis of Compound 20

A solution of 0.1 gram (0.00025 mole) of 1-[4-(3,3-dichloroprop-2-enyloxy)-2,6-dichlorophenoxy]-2-bromoethane, 0.07 gram (0.00038 mole) of (3,4-dichlorophenyl)piperazine (commercially available) and 0.14 gram (0.0001 mole) of potassium carbonate in 3 mL of DMF was warmed to 50° C. where it stirred during an 18 hour period. After this time water was added to the reaction mixture, and the mixture was extracted with diethyl ether. The ether extract was concentrated under reduced pressure to a residue. The residue was purified with column chromatography on silica gel using mixtures of methylene chloride in hexane, and finally 100% methylene chloride, as eluants. The appropriate fractions were combined and concentrated under reduced pressure, yielding Compound 20. The NMR spectrum was consistent with the proposed structure.

EXAMPLE 4

This example illustrates one protocol for the preparation of 4-[4-(3,3-dichloroprop-2-enyloxy)-2,6-dichlorophenyl]piperazinyl 4-(trifluoromethyl)phenyl ketone (Compound 24 in table below)

Step A Synthesis of tert-butyl 4-(2,6-dichloro-4-methoxyphenyl)piperazinecarboxylate as an Intermediate This compound was prepared in a manner analogous to that of Example 2 Step A, by the reaction of 6.8 grams (0.027 mole) of 1,3-dichloro-5-methoxy-2-bromobenzene (known compound), 5.0 grams (0.027 mole) of tert-butyl piperidinecarboxylate, 0.5 gram (0.0005 mole) of tris(dibenzylideneacetone)dipalladium(0), 1.0 gram (0.0006 mole) of racemic-2,2'-bis(diphenylphosphono)-1,1'-binaphthyl, and 4.6 grams (0.048 mole) of sodium tert-butoxide in 250 mL of toluene. The crude reaction product was purified with column chromatography on silica gel using methylene chloride as an eluant. The appropriate fractions were combined and concentrated under reduced pressure, yielding 2.1 grams of the subject compound. The NMR spectrum was consistent with the proposed structure. The reaction was repeated to obtain additional material for the next reactive step.

Step B Synthesis of tert-butyl 4-(2,6-dichloro-4-hydroxyphenyl)piperazinecarboxylate as an Intermediate This compound was prepared in a manner analogous to that of Example 2 Step B, by the reaction of 3.7 grams (0.01 mole) of tert-butyl 4-(2,6-dichloro-4-methoxyphenyl)piperazinecarboxylate and 1.8 grams (0.025 mole) of sodium methanethiolate in 150 mL of DMF. The crude reaction product was purified with column chromatography on silica gel using 50% hexane in methylene chloride, 100% methylene chloride and finally 20% methanol in methylene chloride as eluants. The appropriate fractions were combined and concentrated under reduced pressure, yielding 0.88 gram of the subject compound. The NMR spectrum was consistent with the proposed structure. The reaction was repeated to obtain additional material for the next reactive step.

Step C Synthesis of tert-butyl 4-[4-(3,3-dichloroprop-2-enyloxy)-2,6-dichlorophenyl]piperazinecarboxylate as an Intermediate This compound was prepared in a manner analogous to that of Example 1 Step C, by the reaction of 2.8 grams (0.008 mole) of tert-butyl 4-(2,6-dichloro-4-hydroxyphenyl)piperazinecarboxylate, 2.2 grams (0.012 mole) of 1,1,1,3-tetrachloropropane and 1.7 grams (0.012 mole) of potassium carbonate in 75 mL of DMF. The crude reaction product was purified with column chromatography on silica gel using 50% hexane in methylene chloride and finally 100% methylene chloride as eluants. The appropriate fractions were combined and concentrated under reduced pressure, yielding 0.88 gram of the subject compound. The NMR spectrum was consistent with the proposed structure. The reaction was repeated to obtain additional material for the next reactive step.

Step D Synthesis of 5-(3,3-dichloroprop-2-enyloxy)-1,3-dichloro-2-piperazinylbenzene as an Intermediate Under a nitrogen atmosphere, a stirred solution of 1.8 gram (0.0039 mole) of tert-butyl 4-[4-(3,3-dichloroprop-2-enyloxy)-2,6-dichlorophenyl]piperazinecarboxylate in 30 mL of methylene chloride was cooled to about 0° C. and 0.53 gram (0.0039 mole) of aluminum chloride was added portion-wise. Upon completion of addition the reaction mixture was allowed to warm to ambient temperature where it stirred during a five hour period. After this time 20 mL of an aqueous solution of 10% sodium hydroxide was added dropwise, then the mixture was extracted with two 25 mL portions of ethyl acetate. The combined extracts were washed with one 25 mL portion of an aqueous solution saturated with sodium chloride, dried with sodium sulfate and filtered. The filtrate was concentrated under reduced pressure, yielding 1.2 grams of the subject compound. The NMR spectrum was consistent with the proposed structure.

Step E Synthesis of Compound 24

A stirred solution of 0.15 gram (0.00042 mole) of 5-(3,3-dichloroprop-2-enyloxy)-1,3-dichloro-2-piperazinylbenzene, 0.1 mL (0.00063 mole) of 4-trifluoromethylbenzoyl chloride and 0.15 mL (0.001 mole) of DBU in 8 mL of acetonitrile was warmed to 80° C. where it stirred during an 18 hour period. After this time the reaction mixture was cooled and poured into 25 mL of water, and the mixture was extracted with two 15 mL portions of methylene chloride. The combined extracts were washed with one 15 mL portion of water, dried with sodium sulfate and filtered. The filtrate was concentrated under reduced pressure to a residue. The residue was purified with column chromatography on silica gel using 25% methylene chloride as an eluant. The appropriate fractions were combined and concentrated under reduced pressure, yielding 0.12 gram of Compound 24. The NMR spectrum was consistent with the proposed structure.

EXAMPLE 5

This example illustrates one protocol for the preparation of 5-(3,3-dichloroprop-2-enyloxy)-1,3-dichloro-2-{4-[4-(trifluoromethyl)phenylsulfonyl]piperazinyl}benzene (Compound 26 in table below)

This compound was prepared in a manner analogous to that of Example 4 Step E, by the reaction of 0.15 gram (0.00042 mole) of 5-(3,3-dichloroprop-2-enyloxy)-1,3-dichloro-2-piperazinylbenzene, 0.15 gram (0.00063 mole) of 4-trifluoromethylbenzenesulfonyl chloride (commercially available) and 0.15 mL (0.001 mole) of DBU in 8 mL of acetonitrile. The crude reaction product was purified with column chromatography on silica gel using 1:1 methylene chloride and hexane as an eluant. The appropriate fractions were combined and concentrated under reduced pressure, yielding 0.06 gram of Compound 26. The NMR spectrum was consistent with the proposed structure.

EXAMPLE 6

This example illustrates one protocol for the preparation of 5-(3,3-dichloroprop-2-enyloxy)-1,3-dichloro-2-({1-(trifluoromethyl)(2-pyridyl)](4-piperidyl)}methoxy)benzene (Compound 30 in table below)

Step A Synthesis of ethyl 2-{1-5-(trifluoromethyl)-2-pyridyl]4-piperidyl}acetate as an Intermediate A stirred solution of 5.0 grams (0.032 mole) of 2-chloro-5-trifluoromethylpyridine and 4.9 grams (0.032 mole) of ethyl isonipecotate in 50 mL of acetonitrile as heated to 80° C. where it was maintained during a two-hour period. After this time the reaction mixture was concentrated under reduced pressure to a residue. The residue was dissolved in 50 mL of methylene chloride and washed in turn with an aqueous solution of 10% sodium hydroxide and an aqueous solution saturated with sodium chloride. The organic phase was dried with magnesium sulfate, filtered and the filtrate was concentrated under reduced pressure to a residue. The residue was purified with column chromatography on silica gel using 30% ethyl acetate in heptane as an eluant. The appropriate fractions were combined and concentrated under reduced pressure, yielding 4.2 grams of the subject compound. The NMR spectrum was consistent with the proposed structure.

Step B Synthesis of 1,3-dichloro-5-(phenylmethoxy)-2-({1-[5-(trifluoromethyl)(2-pyridyl)](4-piperidyl)}methoxy)benzene as an intermediate A stirred solution of 4.0 grams (0.0132 mole) of ethyl 2-{1-[5-(trifluoromethyl)-2-pyridyl]-4-piperidyl}acetate in 25 mL of THF was cooled to 10° C. and 10 mL (0.0100 mole) of 1 molar lithium aluminum hydride was added during a five minute period. Upon completion of addition the reaction mixture was stirred for about four hours, after which time the reaction was completed. The reaction mixture was poured into 50 mL of an aqueous solution saturated with ammonium chloride, and the mixture was extracted with two 100 mL portions of diethyl ether. The combined extracts were washed with 50 mL of an aqueous solution saturated with sodium chloride, dried with magnesium sulfate and filtered. The filtrate was concentrated under reduce pressure to a residue, yielding 3.1 grams of the intermediate {1-[5-(trifluoromethyl)-2-pyridyl]4-piperidyl}methan-1-ol. The NMR spectrum was consistent with the proposed structure.

The so-prepared methanol was then dissolved in 100 mL of THF and 2.6 grams (0.01 mole) of triphenylphosphine was added. To this was then added 2.2 grams (0.01 mole) of 2,6-dichloro-4-(phenylmethoxy)phenol (known compound), followed by 1.6 grams (excess) of DEAD. Upon completion of addition the reaction mixture was stirred at ambient temperature for two hours, then it was concentrated under reduced pressure to a residue. The residue was dissolved in methylene chloride and washed in turn with an aqueous solution of 10% sodium hydroxide and an aqueous solution saturated with ammonium chloride. The organic phase was dried with magnesium sulfate, filtered and the filtrate was concentrated under reduced pressure to a residue. The residue was purified with column chromatography on silica gel using 10% ethyl acetate in heptane as an eluant. The appropriate fractions were combined and concentrated under reduced pressure, yielding 2.6 grams of the subject compound. The NMR spectrum was consistent with the proposed structure.

Step C Synthesis of 3,5-dichloro-4-({1-[5-(trifluoromethyl)(2-pyridyl)](4-piperidyl)}methoxy)phenol as an Intermediate This compound was prepared in a manner analogous to that of Example 1 Step B, by the treatment of 2.5 grams (0.0049 mole) of 1,3-dichloro-5-(phenylmethoxy)-2-({1-[5-(trifluoromethyl)(2-pyridyl)](4-piperidyl)}methoxy)benzene with hydrogen gas in the presence of 0.3 gram (catalyst) of 10% palladium on carbon in 25 mL of ethyl acetate and 50 mL of ethanol using a Parr hydrogenation apparatus. The yield of the subject compound was 2.0 grams. The NMR spectrum was consistent with the proposed structure.

Step D Synthesis of Compound 30

This compound was prepared in a manner analogous to that of Example 1 Step C, by the reaction of 2.0 grams (0.0047 mole) of 3,5-dichloro-4-({1-[5-(trifluoromethyl)(2-pyridyl)](4-piperidyl)}methoxy)phenol, 0.90 gram (0.047 mole) of 1,1,1,3-tetrachloropropane and 1.0 gram (excess) of potassium carbonate in 20 mL of DMF. The crude reaction product was purified with column chromatography on silica gel using 15% ethyl acetate in heptane as an eluant. The appropriate fractions were combined and concentrated under reduced pressure, yielding 0.52 gram of Compound 30. The NMR spectrum was consistent with the proposed structure.

EXAMPLE 7

This example illustrates one protocol for the preparation of 1-{2-[4-(3,3-dichloroprop-2-enyloxy)-2,6-dichlorophenoxy]ethyl}-4-(4-chlorophenyl)piperidin-4-ol (Compound 35 in table below)

This compound was prepared in a manner analogous to that of Example 3 step E, by the reaction of 0.1 gram (0.00025 mole) of 1-[4-(3,3-dichloroprop-2-enyloxy)-2,6-dichlorophenoxy]-2-bromoethane, 0.07 gram (0.00033 mole) of 4-(4-chlorophenyl)piperidin-4-ol (commercially available) and 0.20 gram (0.0014 mole) of potassium carbonate in 5 mL of acetone. The crude reaction product was purified with column chromatography on silica gel using 100% methylene chloride and finally 5% methanol in methylene chloride as eluants. The appropriate fractions were combined and concentrated under reduced pressure, yielding 0.07 gram of Compound 35. The NMR spectrum was consistent with the proposed structure.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth some compounds of formula I:

TABLE 1

Insecticidal Phenyl Substituted Cyclic derivatives

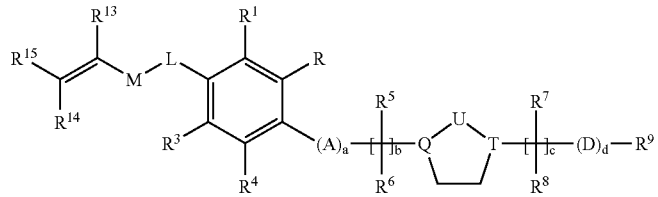

I

Where L is O, M is $CH_2$, $R^{13}$ is hydrogen, and $R^{14}$ and $R^{15}$ are each chlorine; $R^1$ and $R^3$ are hydrogen; R and $R^4$ are chlorine; U is $(CR^a R^b)j$ where $R^a$ and $R^b$ are hydrogen and j is 2 providing compounds of Formula IA as set forth below:

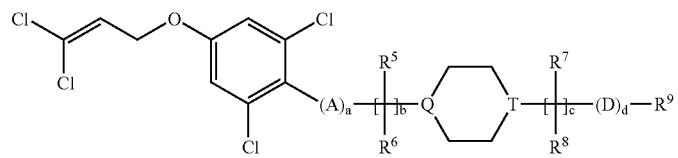

IA

| Cmpd. No. | a/A | b/$R^5$/$R^6$ | Q | T | c/$R^7$/$R^8$ | d/D | $R^9$ |
|---|---|---|---|---|---|---|---|
| 1* | 1/O | 0/–/– | $CR^a$ | N | 0/–/– | 1/C(=O) | $OC_2H_5$ |
| 2* | 1/O | 0/–/– | $CR^a$ | N | 0/–/– | 1/C(=O) | $OC(CH_3)_3$ |
| 3* | 1/$OCH_2$ | 0/–/– | $CR^a$ | N | 0/–/– | 1/C(=O) | $OC_2H_5$ |
| 4* | 1/$OCH_2$ | 0/–/– | $CR^a$ | N | 0/–/– | 1/C(=O) | $OC(CH_3)_3$ |
| 5 | 1/$OCH_2$ | 1/H/H | N | N | 0/–/– | 1/C(=O) | $OC(CH_3)_3$ |
| 6 | 1/$OCH_2$ | 2/H/H | N | N | 0/–/– | 1/C(=O) | $OC(CH_3)_3$ |
| 7 | 0/– | 0/– | N | N | 0/–/– | 1/C(=O) | $OCH_3$ |

TABLE 1-continued

| 8 | 0/– | 0/– | N | N | 0/–/– | 1/C(=O)O | $C_2H_5$ |
| 9 | 0/– | 0/– | N | N | 0/–/– | 1/C(=O)O | $C(CH_3)_3$ |

*where $R^a$ is hydrogen.

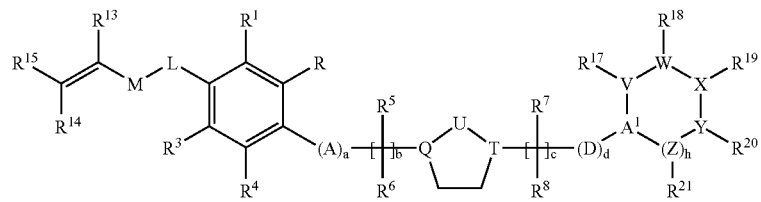

I

Where L is O, M is $CH_2$, $R^{13}$ is hydrogen, and $R^{14}$ and $R^{15}$ are
each chlorine; $R^1$ and $R^3$ are hydrogen; R and $R^4$ are chlorine;
U is $(CR^aR^b)j$ where $R^a$ and $R^b$ are hydrogen
and j is 2; h is 1; $A^1$, W and Y are C=; V, X and Z are C; and $R^{20}$ and $R^{21}$ are
hydrogen providing compounds of Formula IB as set forth below:

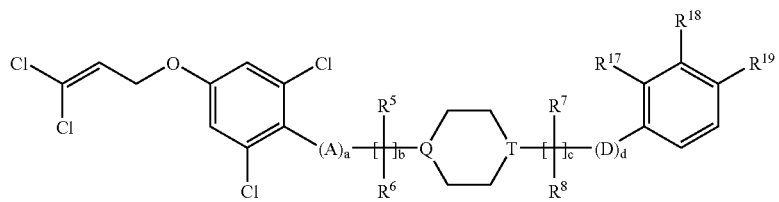

IB

| Cmpd. No. | a/A | b/$R^5$/$R^6$ | Q | T | c/$R^7$/$R^8$ | d/D | $R^{17}$ | $R^{18}$ | $R^{19}$ |
|---|---|---|---|---|---|---|---|---|---|
| 10 | 0/– | 0/–/– | N | N | 0/–/– | 0/– | H | H | F |
| 11 | 0/– | 0/–/– | N | N | 0/–/– | 0/– | H | $CF_3$ | H |
| 12 | 0/– | 0/–/– | N | N | 0/–/– | 0/– | H | H | $CF_3$ |
| 13 | 0/– | 0/–/– | N | N | 1/H/H | 0/– | H | H | $CF_3$ |
| 14** | 1/O | 0/–/– | $CR^a$ | N | 1/H/H | 0/– | H | H | $CF_3$ |
| 15** | 1/O | 1/H/H | $CR^a$ | N | 1/H/H | 0/– | H | H | $CF_3$ |
| 16 | 1/$OCH_2$ | 1/H/H | N | N | 0/–/– | 0/– | Cl | H | H |
| 17 | 1/$OCH_2$ | 1/H/H | N | N | 0/–/– | 0/– | H | Cl | H |
| 18 | 1/$OCH_2$ | 1/H/H | N | N | 0/–/– | 0/– | H | H | Cl |
| 19 | 1/$OCH_2$ | 1/H/H | N | N | 0/–/– | 0/– | Cl | Cl | H |
| 20 | 1/$OCH_2$ | 1/H/H | N | N | 0/–/– | 0/– | H | Cl | Cl |
| 21 | 1/$OCH_2$ | 1/H/H | N | N | 0/–/– | 0/– | $CH_3$ | H | $CH_3$ |
| 22 | 1/$OCH_2$ | 1/H/H | N | N | 0/–/– | 0/– | H | H | $CF_3$ |
| 23** | 0/– | 0/–/– | N | $CR^a$ | 0/–/– | 1/O | H | H | $CF_3$ |
| 24 | 0/– | 0/–/– | N | N | 0/–/– | 1/C(=O) | H | H | $CF_3$ |
| 25 | 0/– | 0/–/– | N | N | 0/–/– | 1/C(=O)NH | H | H | $CF_3$ |
| 26[1] | 0/– | 0/–/– | N | N | 0/–/– | 1/$S(O)_g$ | H | H | $CF_3$ |
| 27 | 0/– | 1/H/H | N | N | 1/H/H | - 0/– | H | H | $CF_3$ |

**where $R^a$ is hydrogen; [1]where g is 2

TABLE 1-continued

Where L is O, M is CH$_2$, R$^{13}$ is hydrogen, and R$^{14}$ and R$^{15}$ are each chlorine; R$^1$ and R$^3$ are hydrogen; R and R$^4$ are chlorine; U is (CR$^a$R$^b$)j where R$^a$ and R$^b$ are hydrogen and j is 2; h is 1; A$^1$, W and Y are C=; V, X and Z are are C; where R$^{17}$ and R$^{18}$, or R$^{18}$ and R$^{19}$ are taken together to form a fused ring; and R$^{20}$ and R$^{21}$ are hydrogen providing compounds of Formula IC as set forth below:

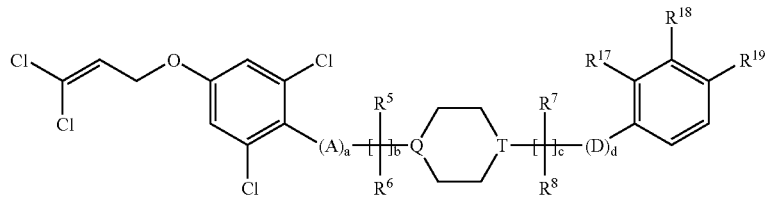

IC

| Cmpd. No. | a/A | b/R$^5$/R$^6$ | Q | T | c/R$^7$/R$^8$ | d/D | R$^{17}$ | R$^{18}$ | R$^{19}$ | R$^{22}$ | R$^{23}$ |
|---|---|---|---|---|---|---|---|---|---|---|---|
| 28* | 0/– | 0/– | N | CR$^a$ | 0/– | 1/O | OCR$^{22}$R$^{23}$CH$_2$ | H | CH$_3$ | CH$_3$ | |

*where R$^a$ is hydrogen

Where L is O, M is CH$_2$, R$^{13}$ is hydrogen, and R$^{14}$ and R$^{15}$ are each chlorine; R$^1$ and R$^3$ are hydrogen; R and R$^4$ are chlorine; U is (CR$^a$R$^b$)j where R$^a$ and R$^b$ are hydrogen; b and c are 0; h is 1; A$^1$, W and Y are C=; V is N; X and Z are are C; and R$^{17}$, R$^{18}$, R$^{20}$ and R$^{21}$ are hydrogen providing compounds of Formula ID as set forth below:

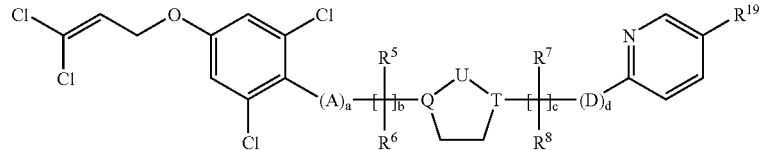

ID

| Cmpd. No. | a/A | Q | j | T | d/D | R$^{19}$ |
|---|---|---|---|---|---|---|
| 29* | 1/O | CR$^a$ | 2 | N | 0/– | CF$_3$ |
| 30* | 1/OCH$_2$ | CR$^a$ | 2 | N | 0/– | CF$_3$ |
| 31 | 0/– | N | 2 | N | 0/– | CF$_3$ |
| 32 | 1/CH$_2$ | N | 2 | N | 0/– | CF$_3$ |
| 33 | 1/OCH$_2$ | N | 2 | N | 0/– | H |
| 34 | 1/OCH$_2$ | N | 2 | N | 0/– | CF$_3$ |

*where R$^a$ is hydrogen

Where L is O, M is CH$_2$, R$^{13}$ is hydrogen, and R$^{14}$ and R$^{15}$ are each chlorine; R$^1$ and R$^3$ are hydrogen; R and R$^4$ are chlorine; U is (CR$^a$R$^b$)j where R$^a$ and R$^b$ are hydrogen and j is 2; c and d are 0 and h is 1; A$^1$, W and Y are C=; V, X and Z are C; and R$^{17}$, R$^{18}$, R$^{20}$ and R$^{21}$ are hydrogen providing compounds of Formula IE as set forth below:

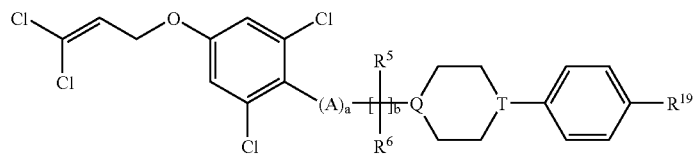

IE

| Cmpd. No. | a/A | b/R$^5$/R$^6$ | Q | T | R$^a$ | R$^{19}$ |
|---|---|---|---|---|---|---|
| 35 | 1/OCH$_2$ | 1/H/H | N | CR$^a$ | OH | Cl |

The following table sets forth physical characterizing data for certain compounds of formula I of the present invention. The test compounds of formula I are identified by numbers that correspond to those in Table 1:

TABLE 2

Insecticidal Phenyl Substituted Cyclic Derivatives
Compound Characterization
Characterizing Data

| Cmpd. No. | Emperical Formulae | Physical State | Cmpd. No. | Emperical Formulae | Physical State |
|---|---|---|---|---|---|
| 1 | $C_{17}H_{19}Cl_4NO_4$ | Oil | 2 | $C_{19}H_{23}Cl_4NO_4$ | Oil |
| 3 | $C_{18}H_{21}Cl_4NO_4$ | Oil | 4 | $C_{20}H_{25}Cl_4NO_4$ | Oil |
| 5 | $C_{20}H_{26}Cl_4N_2O_4$ | Oil | 6 | $C_{17}H_{19}NO_5$ | — |
| 7 | $C_{15}H_{16}Cl_4N_2O_3$ | Liquid | 8 | $C_{16}H_{18}Cl_4N_2O_3$ | Liquid |
| 9 | $C_{18}H_{22}Cl_4N_2O_3$ | Liquid | 10 | $C_{19}H_{17}Cl_4FN_2O$ | Liquid |
| 11 | $C_{20}H_{17}Cl_4F_3N_2O$ | Liquid | 12 | $C_{20}H_{17}Cl_4F_3N_2O$ | Solid (111-113° C.) |
| 13 | $C_{21}H_{19}Cl_4F_3N_2O$ | Liquid | 14 | $C_{22}H_{20}Cl_4F_3NO_2$ | Oil |
| 15 | $C_{23}H_{22}Cl_4F_3NO_2$ | Oil | 16 | $C_{21}H_{21}Cl_5N_2O_2$ | Oil |
| 17 | $C_{21}H_{21}Cl_5N_2O_2$ | Oil | 18 | $C_{21}H_{21}Cl_5N_2O_2$ | Oil |
| 19 | $C_{21}H_{20}Cl_6N_2O_2$ | Oil | 20 | $C_{21}H_{20}Cl_6N_2O_2$ | Oil |
| 21 | $C_{23}H_{26}Cl_4N_2O_2$ | Oil | 22 | $C_{22}H_{21}Cl_4F_3N_2O_2$ | Oil |
| 23 | $C_{21}H_{18}Cl_4F_3NO_2$ | Liquid/Oil | 24 | $C_{21}H_{17}Cl_4F_3N_2O_2$ | Liquid |
| 25 | $C_{21}H_{18}Cl_4F_3N_3O_2$ | Solid (127-130° C.) | 26 | $C_{20}H_{17}Cl_4F_3N_2O_3S$ | Liquid |
| 27 | $C_{22}H_{21}Cl_4F_3N_2O$ | Liquid | 28 | $C_{24}H_{25}Cl_4NO_3$ | Liquid |
| 29 | $C_{20}H_{17}Cl_4F_3N_2O_2$ | Oil | 30 | $C_{21}H_{19}Cl_4F_3N_2O_2$ | Oil |
| 31 | $C_{19}H_{16}Cl_4F_3N_3O$ | Solid | 32 | $C_{20}H_{18}Cl_4F_3N_3O$ | Liquid |
| 33 | $C_{20}H_{21}Cl_4N_3O_2$ | Oil | 34 | $C_{21}H_{20}Cl_4F_3N_3O_2$ | Oil |
| 35 | $C_{22}H_{22}Cl_5NO_3$ | Oil | | | |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID#430345-15.5 mm dia.×17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Certain Phenyl Substituted Cyclic Derivatives
When Applied to the Surface of the Diet of Tobacco Budworm
(*Heliothis virescens* [Fabricius])

| Cmpd. No. | Percent Mortality | Percent Growth Inhibition | Cmpd. No. | Percent Mortality | Percent Growth Inhibition |
|---|---|---|---|---|---|
| 2 | 100 | 100 | 3 | 100 | 100 |
| 4 | 100 | 100 | 5 | 100 | 100 |
| 7 | 100 | 100 | 8 | 100 | 100 |
| 9 | 100 | 100 | 11 | 100 | 100 |
| 12 | 100 | 100 | 14 | 100 | 100 |
| 15 | 100 | 100 | 16 | 100 | 100 |
| 17 | 100 | 100 | 18 | 100 | 100 |
| 19 | 100 | 100 | 20 | 100 | 100 |
| 21 | 100 | 100 | 22 | 100 | 100 |
| 23 | 100 | 100 | 24 | 100 | 100 |
| 25 | 100 | 100 | 26 | 100 | 100 |
| 27 | 100 | 100 | 28 | 100 | 100 |
| 29 | 100 | 100 | 30 | 100 | 100 |
| 31 | 100 | 100 | 32 | 100 | 100 |
| 33 | 100 | 100 | 34 | 100 | 100 |
| 35 | 100 | 100 | | | |

Concentration of the candidate insecticide on the surface of the diet is 0.25 millimolar As set forth in Table 3, all of the compounds of the present invention tested provided 100% mortality and 100% growth inhibition of the tobacco budworm.

As set forth above, the present invention also includes novel intermediates finding utility in the syntheses of compounds of formula I. Those intermediates are as follows, and are designated as compounds of formula II:

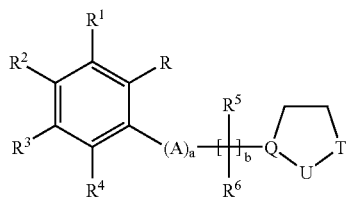

II where
— R is hydrogen, halogen or ($C_1$-$C_3$)alkyl;
$R^2$ is selected from hydroxy, phenylmethoxy and -L-M-C($R^{13}$)=C($R^{14}$)($R^{15}$) where L is O, M is (CH$_2$)$_f$ where f is 1, $R^{13}$ is hydrogen; and $R^{14}$ and $R^{15}$ are each chlorine;
— $R^1$ and $R^3$ are independently selected from hydrogen or halogen;
— $R^4$ is halogen or ($C_1$-$C_3$)alkyl;
-a is an integer selected from 0 or 1, and when a is 1, A is OCH$_2$;
-b is an integer selected from 0, 1, 2, 3 or 4, and when b is 1 or more, $R^5$ and $R^6$ are each hydrogen;
-Q is selected from —N—; —N$^+$H(X$^-$)—, where X$^-$ is an anion selected from halide, sulfate, carbonate, bicarbonate, nitrate, perchlorate, formate, acetate and trihaloacetate; and —CR$^a$— where R$^a$ is hydrogen;
-T is selected from —NR$^a$, where R$^a$ is selected from hydrogen, formyl, acetyl, alkoxycarbonyl, alkenyloxycarbonyl, benzoyl, benzyloxycarbonyl, alkanesulfonyl, benzenesulfonyl and toluenesulfonyl; —N$^+$H(X$^-$)—, where X$^-$ is as previously described; and —CR$^a$R$^b$ where R$^a$ and R$^b$ are independently selected from hydrogen, hydroxy and ($C_1$-$C_6$)alkoxy; and R$^a$ and R$^b$ may be taken together with O to form a carbonyl group, or may be taken together with —O($C_2$-$C_3$)alkoxy- or —S($C_2$-$C_3$)alkylthio- to form a ketal or thioketal, respectively; provided that at least one of Q or T is —N— or —N$^+$H(X$^-$)—;

and
—U is —(CR$^a$R$^b$)$_j$—, where R$^a$ and R$^b$ are hydrogen and j is 2.

Preferred amongst the compounds of formula II are those where R and R$^4$ are each chlorine; $R^1$ and $R^3$ are each hydrogen; $R^2$ is -L-M-C($R^{13}$)=C($R^{14}$)($R^{15}$); b is an integer selected from 0, 1 or 2; and T is —NR$^a$ where R$^a$ is hydrogen or tert-butoxycarbonyl; and more preferably those compounds where i) a and b are 0, Q is N, and T is —NR$^a$ where R$^a$ is hydrogen; ii) a is 1, b is 0, Q is —CR$^a$— and T is NR$^a$ where R$^a$ is hydrogen; and iii) a is 1, b is 1 or 2 and Q is N and T is —NR$^a$ where R$^a$ is hydrogen.

The synthesis routes set forth below for the preparation of compounds of formula II employ reaction procedures and work-up and purification methods commonly encountered in the organic and chemical literature, and such as taught in Example 1 through Example 7 above. Scheme 6 set forth below depicts one method for the preparation of intermediate compounds of formula II where, for example Q and T are N, and U is —(CR$^a$R$^b$)$_j$—, where R$^a$ and R$^b$ are hydrogen and j is 2:

Scheme 6

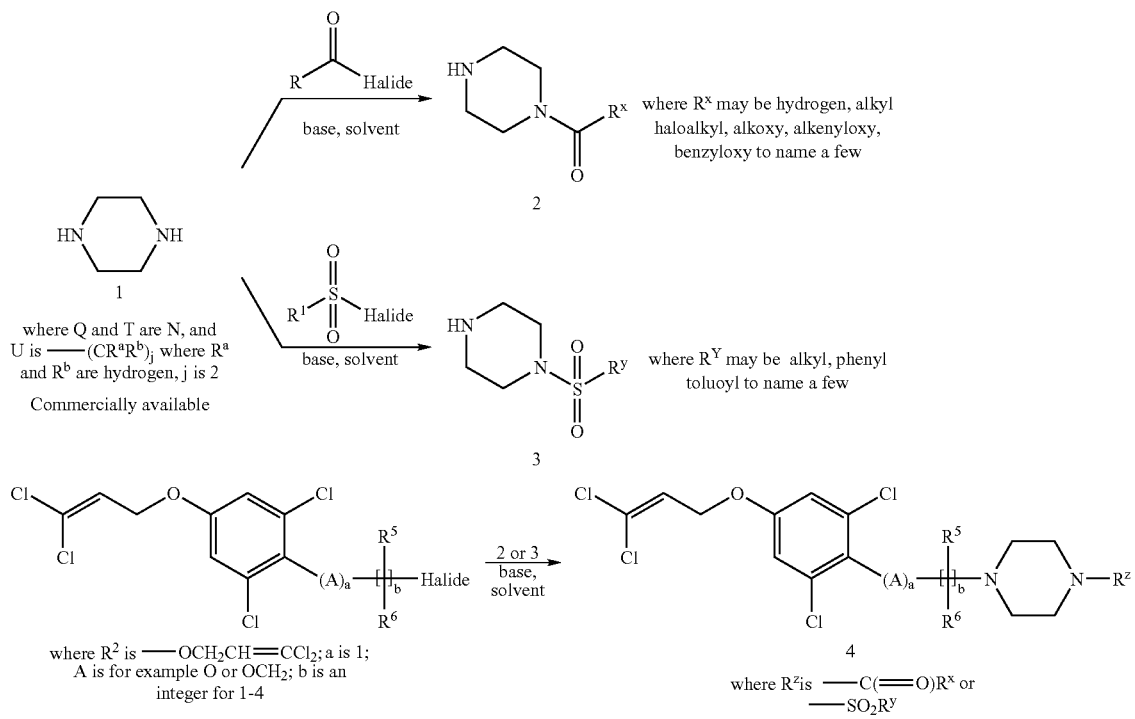

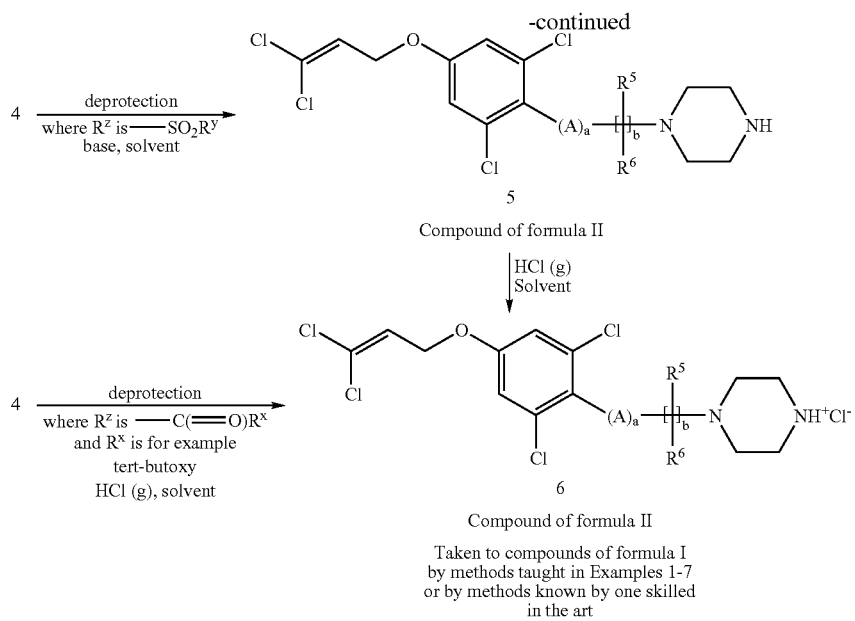

As depicted in Scheme 6, the commercially available piperazine 1 is treated with an acid halide or a sulfonyl halide as a means of protecting one of the amino groups in 1. the so-protected piperazine intermediates 2 and 3 are in turn reacted with a second halide derivative such as 1-[4-(3,3-dichloroprop-2-enyloxy)-2,6-dichlorophenoxy]-2-bromoethane, affording the corresponding piperazine intermediate 4. Deprotection of 4 where $R^z$ is —SO$_2$R$^y$ is accomplished under basic conditions, yielding the corresponding free amine 5, which in turn may be converted to a salt such as a hydrochloride salt 6. Alternatively, where $R^z$ is —C(=O)R$^x$, deprotection of 4 is accomplished under acidic conditions, which yields the salt 6 directly.

Scheme 7 set forth below depicts another method for the preparation of intermediate compounds of formula II where, for example Q and T are N, and U is —(CR$^a$R$^b$)$_j$—, where R$^a$ and R$^b$ are hydrogen and j is 2:

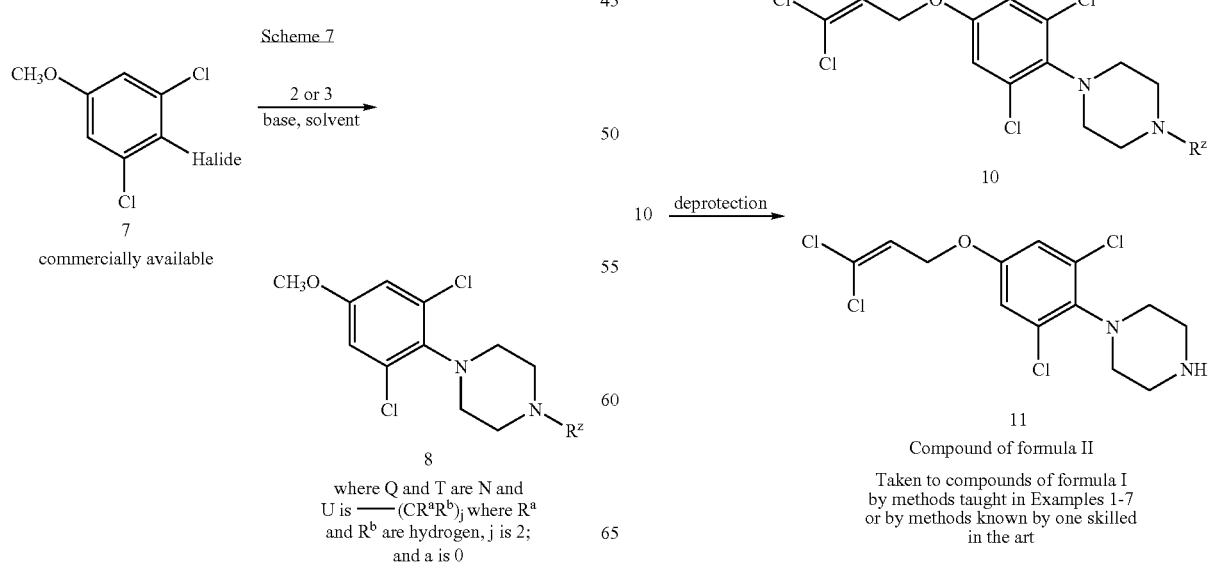

As depicted in Scheme 7, the commercially available phenyl halide 7, for example 1,3-dichloro-5-methoxy-2-bromobenzene, is reacted with either of the piperazine intermediates 2 or 3 as shown in Scheme 6, affording the corresponding piperazine intermediate 8. Intermediate 8 is in turn dealkylated, yielding the phenol intermediate 9. Intermediate 9 is then reacted with, for example 1,1,1,3-tetrachloropropane, affording intermediate 10, which is then deprotected by removal of the moiety $R^z$ by methods set forth above, yielding intermediate 11. Intermediate 11 may optionally be converted to a salt if needed, also using methods set forth above.

Scheme 8 set forth below depicts one method for the preparation of intermediate compounds of formula II where, for example Q is N and T is $CR^a$ and U is —$(CR^aR^b)_j$—, where $R^a$ and $R^b$ are hydrogen and j is 2:

Scheme 8

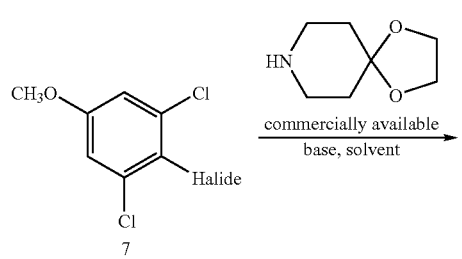

7

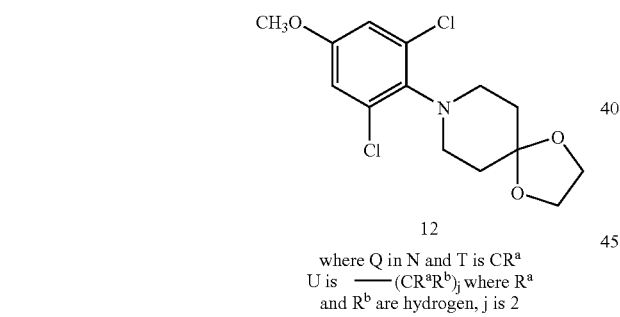

12 where Q in N and T is $CR^a$
U is ——$(CR^aR^b)_j$ where $R^a$
and $R^b$ are hydrogen, j is 2
and a is 0

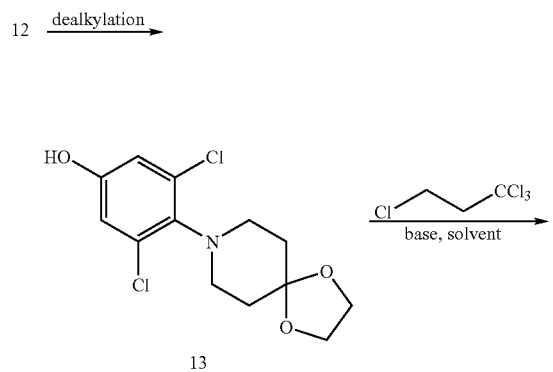

13

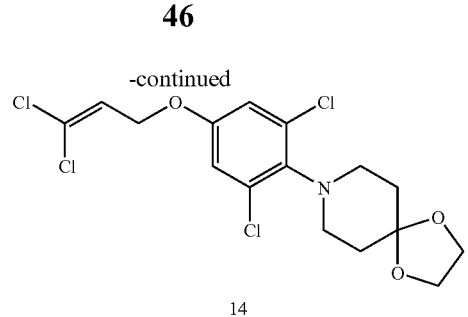

14

14 → deprotection

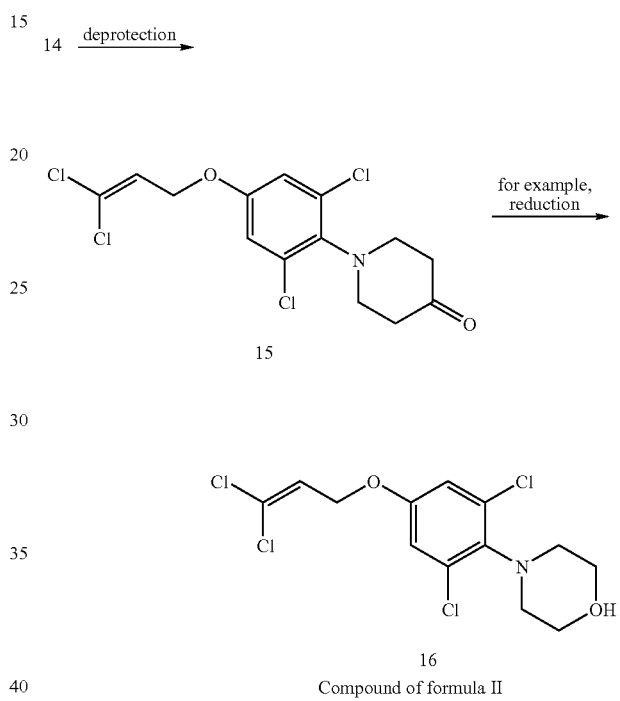

15

16
Compound of formula II

Taken to compounds of formula I
by methods taught in Examples 1-7
or by methods known by one skilled in
the art As depicted in Scheme 8, the commercially available phenyl halide 7, as set forth in Scheme 6, is reacted with, for example the commercially available 1,4-dioxa-8-azaspiro[4.5]decane, yielding the corresponding 4-alkoxyphenyl substituted piperidine 12. Intermediate 12 is then dealkylated, affording the corresponding phenol intermediate 13, which is in turn reacted with for example 1,1,1,3-tetrachloropropane, affording intermediate 14. Intermediate 14 is then deprotected yielding the corresponding ketone 15, for example 1-[4-(3,3-dichloroprop-2-enyloxy)-2,6-dichlorophenyl]piperidin-4-one. Intermediate 15 then may, for example be reduced to provide the corresponding hydroxy intermediate 16.

Scheme 9 set forth below depicts one method for the preparation of intermediate compounds of formula II where, for example is T is N and Q is $CR^a$ and U is —$(CR^aR^b)_j$—, where $R^a$ and $R^b$ are hydrogen and j is 2:

Scheme 9
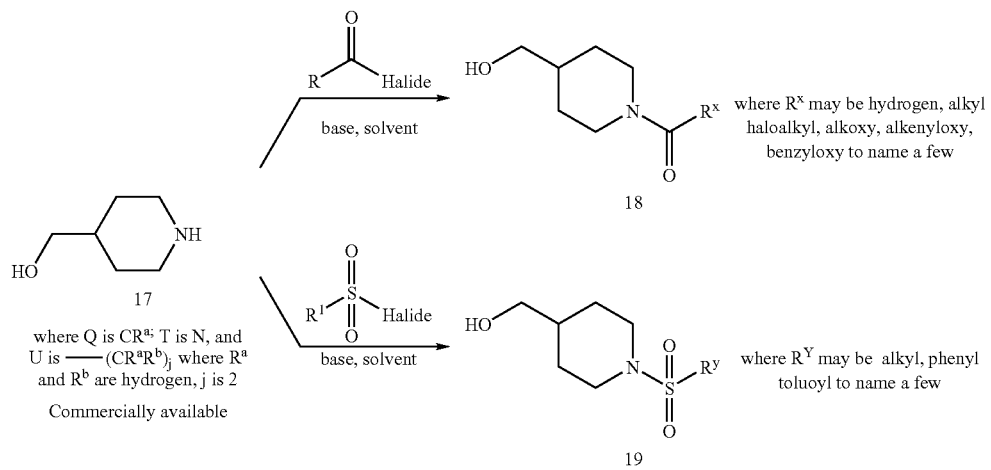
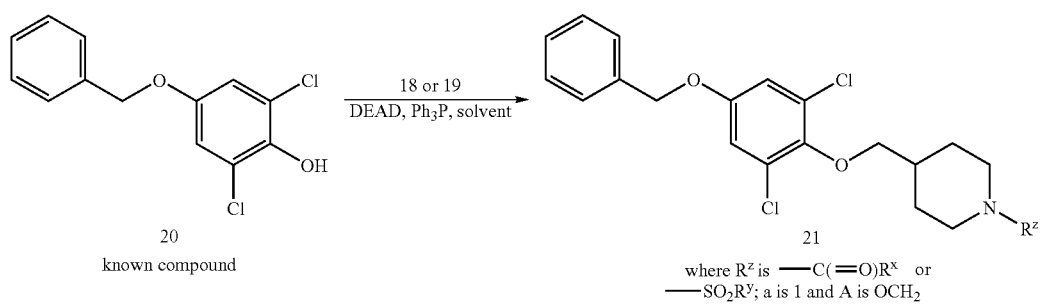
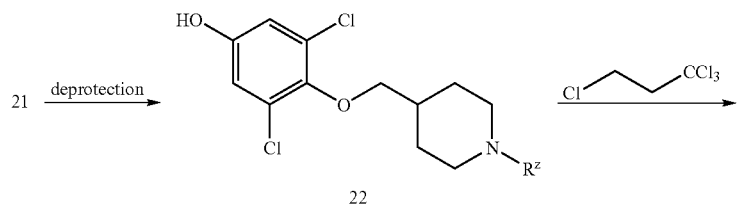
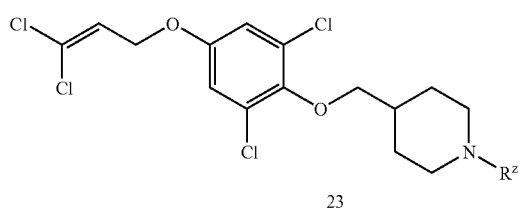
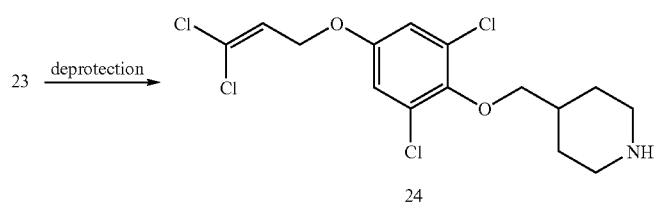
24
Compound of formula II
Taken to compounds of formula I
by methods taught in Examples 1-7
or by methods known by one skilled
in the art As depicted in Scheme 9, for example the commercially available 4-piperidylmethan-1-ol 17 is treated with an acid halide or a sulfonyl halide as shown in Scheme 6, a means of protecting the amino group in 17, affording the corresponding piperidine intermediates 18 and 19. Intermediates 18 and 19 are then reacted with, for example the known compound 2,6-dichloro-4-(phenylmethoxy)phenol 20, providing the corresponding piperidine intermediate 21. Intermediate 21 is then deprotected by removal of the phenylmethyl moiety, affording the corresponding phenol intermediate 22, which is in turn reacted with, for example 1,1,1,3-tetrachloropropane, yielding intermediate 23. Intermediate 23 is then deprotected by methods set forth above, providing the free piperidine intermediate 25. Intermediate 25 may optionally be converted to a salt if needed, also using methods set forth above.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula:

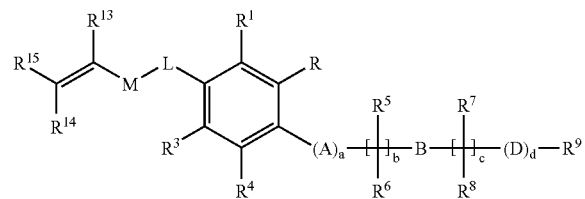

where
— R and $R^4$ are independently selected from hydrogen, halogen, and $(C_1-C_6)$alkyl;
— $R^1$ and $R^3$ are independently selected from hydrogen, halogen and $(C_1-C_3)$alkyl;
-L is selected from O and S;
-M is $(CH_2)_f$ where f is an integer selected from 1, 2 and 3;
— $R^{13}$ is hydrogen;
$R^{14}$ and $R^{15}$ are independently selected from halogen;
-a is an integer selected from 0 or 1;
  and when a is 1,
-A is O;
-b is an integer selected from 0, 1, 2, 3, or 4;
  and when b is 1 or more,
— $R^5$ and $R^6$ are independently selected from hydrogen, halogen, $(C_1-C_4)$alkyl, cyclo$(C_3-C_6)$alkyl, halo$(C_1-C_4)$alkyl, or aryl;
— B is a cyclic bridging group of the structure;

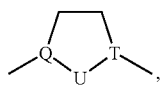

where,
Q and T are independently selected from —CH— and —N—, provided that at least one of Q or T is —N—; and
U is —$(CH_2)_2$—
-c is an integer selected from 0, 1, 2, 3 or 4;
  and when c is 1 or more, — $R^7$ and $R^8$ are independently selected from hydrogen, $(C_1-C_4)$alkyl, halo$(C_1-C_4)$alkyl or $(C_1-C_4)$alkoxy, or aryl;
-d is an integer selected from 0 or 1; and,
when d is 1,
-D is selected from O, CH=CH, S(O)$_g$, HC=N, C(=O), OC(=O), and C(=O)O, C(O)NH, $NR^{16}$, N(oxide)$R^{16}$ and $NR^{16}C$(=O) where g is an integer selected from 0, 1 or 2 and $R^{16}$ selected from hydrogen, $(C_1-C_3)$ alkyl, $(C_1-C_3)$alkoxy$(C_1-C_3)$alkyl, aryl$(C_1-C_3)$alkyl, $(C_2-C_4)$ alkenyl$(C_1-C_3)$alkyl, halo$(C_2-C_4)$alkenyl$(C_1-C_3)$alkyl, di$(C_1-C_3)$alkylphosphonate, $(C_1-C_3)$alkylcarbonyl, halo$(C_1-C_3)$alkylcarbonyl, $(C_1-C_3)$alkoxy $(C_1-C_3)$alkylcarbonyl, arylcarbonyl and $(C_1-C_3)$ alkylsulfonyl; and
— $R^9$ is $(C_1-C_4)$alkoxy; and-a radical of the formula:

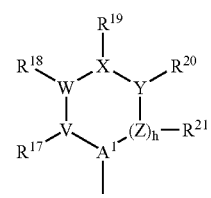

wherein h is 1;
$A^1$, W and Y are selected from C= and N; and
V, X and Z are selected from C and N;
With the proviso that either all of $A^1$, W, Y, V, X and Z are C; or only one of $A^1$, W, Y, V, X and Z is N;
$R^{17}$, $R^{18}$, $R^{19}$, $R^{20}$ and $R^{21}$ are independently selected from hydrogen, halogen, $(C_1-C_3)$alkyl and halo$(C_1-C_3)$alkyl; and
agriculturally-acceptable salts thereof.

2. A compound of claim 1, wherein R and $R^4$ are independently selected from halogen and $(C_1-C_3)$alkyl; L is O; f is 1; $R^{14}$ and $R^{15}$ are independently selected from chlorine and bromine; b is an integer selected from 0, 1, 2, 3 or 4, and when b is 1 or more, $R_5$ and $R_6$ are each hydrogen;
c is an integer selected from 0, 1, 2, 3 or 4, and when c is 1 or more, $R^7$ and $R^8$ are hydrogen; when d is 1; and D is selected from C(=O), C(=O)NH and S(O)$_g$ where g is 2.

3. A compound of claim 2, wherein R and $R^4$ are each chlorine; $R^1$ and $R^3$ are each hydrogen; b is an integer selected from 0 or 1; T is N; c is an integer selected from 0 or 1; d is 0 or 1; and when d is 1, -D is C(=O) or S(O)$_g$.

4. A compound of claim 3, wherein c is 0; d is an integer selected from 0 or 1, and when d is 1, D is S(O)$_g$; $R^{21}$ is hydrogen; and $R^{17}$ through $R^{20}$, inclusively, are independently selected from hydrogen, chlorine and trifluoromethyl.

5. A composition comprising an insecticidally effective amount of a compound of claim 1 in admixture with at least one agriculturally acceptable extender or adjuvant.

6. The insecticidal composition of claim 5, further comprising one or more second compounds selected from the group consisting of pesticides, plant growth regulators, fertilizers and soil conditioners.

7. A compound of formula I

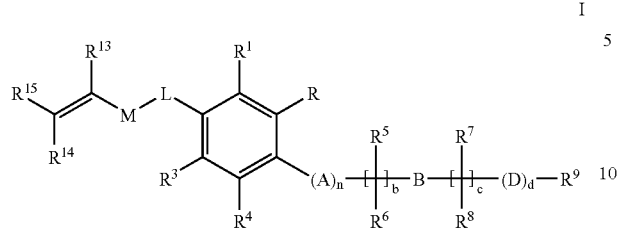

where
- R and $R^4$ are independently selected from hydrogen, halogen or $(C_1$-$C_3)$alkyl;
- $R^1$ and $R^3$ are hydrogen;
- L is 0; M is $(CH_2)_f$ where f is 1; and $R^{14}$ and $R^{15}$ are each chlorine;
- a is an integer selected from 0 or 1;
  and when a is 1,
- A is O;
- b is an integer selected from 0, 1, 2, 3 or 4;
  and when b is 1 or more,
- $R^5$ and $R^6$ are each hydrogen;
- B is a cyclic bridging group of the structure,

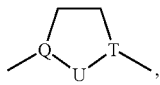

where
  Q and T are independently selected from —$CR^a$— and —N—, provided that at least one of Q or T is —N—; where $R^a$ is hydrogen; U is —$(CR^aR^b)_j$-, where $R^a$ and $R^b$ are hydrogen and j is 2;
- c is an integer selected from 0, 1, 2, 3 or 4;
  and when c is 1 or more,
- $R^7$ and $R^8$ are hydrogen;
- d is an integer selected from 0 or 1;
  and when d is 1,
- D is selected from O, C(=O), C(=O)NH and $S(O)_g$ where g is 2;
- $R^2$ is selected from $(C_1$-$C_4)$alkoxy and a radical of the formula:

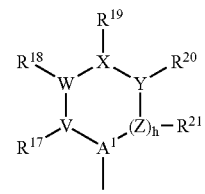

where
  - h is 1;
  - $A^1$, W and Y are selected from C= and N; and
  - V, X and Z are selected from C and N;
  - With the proviso that either all of $A^1$, W, Y, V, X and Z are or only one of $A^1$, W, Y, V, X and Z is N;
  - $R^{17}$, $R^{18}$, $R^{19}$, $R^{20}$ and $R^{21}$ are independently selected from hydrogen, halogen, $(C_1$-$C_3)$alkyl, and halo$(C_1$-$C_3)$alkyl;
  and
  agriculturally acceptable salts thereof.

8. A compound of claim 7, wherein R and $R^4$ are each chlorine; b is an integer selected from 0 or 1; and T is N; c is an integer selected from 0 or 1; d is 0 or 1, and when d is 1, D is C(=O), or $S(O)_g$.

9. A compound of claim 8, wherein c is 0; d is an integer selected from 0 or 1, and when d is 1, D is $S(O)_g$; $R^{21}$ is hydrogen; and $R^{17}$ through $R^{20}$, inclusively, are independently selected from hydrogen, chlorine and trifluoromethyl.

10. A composition comprising an insecticidally effective amount of a compound of claim 7 in admixture with at least one agriculturally acceptable extender or adjuvant.

* * * * *

UNITED STATES PATENT AND TRADEMARK OFFICE
CERTIFICATE OF CORRECTION

| | |
|---|---|
| PATENT NO. | : 7,671,201 B2 |
| APPLICATION NO. | : 10/554328 |
| DATED | : March 2, 2010 |
| INVENTOR(S) | : George Theodoridis et al. |

Page 1 of 1

It is certified that error appears in the above-identified patent and that said Letters Patent is hereby corrected as shown below:

Column 50, line 10, insert --is-- after "R16"
Column 52, line 23, insert --C;-- before "or only one"

Signed and Sealed this
Twenty-eighth Day of December, 2010

David J. Kappos
*Director of the United States Patent and Trademark Office*